(12) United States Patent
Amiss et al.

(10) Patent No.: US 8,778,635 B2
(45) Date of Patent: Jul. 15, 2014

(54) THERMOSTABLE PROTEINS AND METHODS MAKING AND USING THEREOF

(71) Applicant: Becton, Dickinson and Company, Franklin Lakes, NJ (US)

(72) Inventors: Terry J. Amiss, Raleigh, NC (US); Erin M. Gill, Madison, WI (US); Douglas Byron Sherman, Durham, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/950,089

(22) Filed: Jul. 24, 2013

(65) Prior Publication Data

US 2013/0302908 A1 Nov. 14, 2013

Related U.S. Application Data

(62) Division of application No. 11/738,442, filed on Apr. 20, 2007, now Pat. No. 8,623,639.

(60) Provisional application No. 60/745,277, filed on Apr. 20, 2006.

(51) Int. Cl.
| | | |
|---|---|---|
| *C07H 21/04* | (2006.01) | |
| *C12N 1/20* | (2006.01) | |
| *C12N 15/00* | (2006.01) | |
| *C12P 21/06* | (2006.01) | |

(52) U.S. Cl.
USPC .................. 435/69.1; 435/252.33; 435/320.1; 536/23.1

(58) Field of Classification Search
None
See application file for complete search history.

(56) References Cited

U.S. PATENT DOCUMENTS

| | | |
|---|---|---|
| 6,197,534 B1 | 3/2001 | Lakowicz et al. |
| 6,277,627 B1 | 8/2001 | Hellinga |
| 6,288,214 B1 | 9/2001 | Hook et al. |
| 6,403,337 B1 | 6/2002 | Bailey et al. |
| 6,521,446 B2 | 2/2003 | Hellinga |
| 6,576,430 B1 | 6/2003 | Hsieh et al. |
| 6,855,556 B2 | 2/2005 | Amiss et al. |
| 7,064,103 B2 | 6/2006 | Pitner et al. |
| 7,316,909 B2 | 1/2008 | Pitner et al. |
| 7,496,392 B2 | 2/2009 | Alarcon et al. |
| 8,623,639 B2 | 1/2014 | Amiss et al. |
| 2002/0004217 A1 | 1/2002 | Hellinga |
| 2005/0014290 A1 | 1/2005 | Hsieh et al. |
| 2006/0078908 A1 | 4/2006 | Pitner et al. |
| 2006/0216753 A1 | 9/2006 | Pitner et al. |
| 2007/0281368 A1 | 12/2007 | Hsieh et al. |

FOREIGN PATENT DOCUMENTS

| | | |
|---|---|---|
| WO | 99/34212 | 7/1999 |
| WO | 03/057850 | 7/2003 |
| WO | 2007/124464 | 11/2007 |

OTHER PUBLICATIONS

Buhr et al., "The Glucose Transporter of *Escherichia coli*," Journal of Biological Chemistry and Molecular Biology, 269 (38): 23437-23443 (1994).
Burg et al., "Selection of Mutations for Increased Protein Stability," Curr. Opin. in Biotech., 13: 333-337 (2002).
Cuneo et al., "Crystal structure of a disulfide mutant glucose binding protein," RCSB Protein Data Bank, PDB ID 2ipn. Mar. 20, 2007.
Cuneo et al., "Crystal structure of a disulfide mutant glucose binding protein," RCSB Protein Data Bank, PDB ID 2ipm. Mar. 20, 2007.
Cuneo et al., "Crystal structure of a disulfide mutant glucose binding protein," RCSB Protein Data Bank, PDB ID 2ipl. Mar. 20, 2007.
de Lorimier et al., "Construction of a fluorescent biosensor family," Protein Sci., 11(11): 2655-2675 (2002).
Dwyer et al., "Periplasmic binding proteins: a versatile superfamily for protein engineering," Curr. Opin. Struct. Biol., 14 (4): 495-504 (2004).
Herman et al., "The Role of Calcium in the Conformational Dynamics and Thermal Stability of the D-galactose/D-glucose-binding Protein from *Escherichia coli*," Proteins, 61(1): 154-195 (2005).
Lehman et al., "Engineering proteins for thermostability: the use of sequence alignments versus rational design and directed evolution," Curr. Opin. in Biotech., 12: 371-375 (2001).
Lehmann et al., "The Consensus Concept for Thermostability engineering of Proteins: Further Proof of Concept," Protein Eng., 15(5): 403-411 (2002).
Marvin et al., "Engineering Biosensors by Introducing Fluorescent Allosteric Signal Transducers: Construction of a Novel Glucose Sensor," J. Am. Chem. Soc., 120: 7-11 (1998).
Marvin et al., "The Rational Design of Allosteric interactions in a Monomeric Protein and its Applications to the Construction of Biosensors," Proc. Natl. Acad. Sci. USA, 94: 4366-4371 (1997).
Miles et al., "Synchrotron Radiation Circular Dichroism Spectroscopy of Proteins and Applications in Structural and Functional Genomics," Chem. Soc. Rev., 35: 39-51 (2006).
Quiocho et al., "Atomic structure and specificity of bacterial periplasmic receptors for active transport and chemotaxis: variation of common themes," Molecular Microbiology 20(1): 17-25 (1996).
Supplemental European Search Report for European Patent Application No. 07761071.5, Jan. 4, 2010.
Xie et al., "Secondary Structure and Protein Deamidation," Journal of Pharmaceutical Sciences, 88(1): 8-13 (1999).

*Primary Examiner* — Nashaat Nashed
(74) *Attorney, Agent, or Firm* — Morgan Lewis & Bockius LLP

(57) ABSTRACT

The present invention relates to functional, modified glucose-galactose binding proteins (GGBPs), that have a greater melting temperature ($T_m$) than a reference GGBP. The present invention also relates to biological sensors, e.g., glucose sensors, comprising these thermostable GGBPs. The present invention also relates to nucleic acids encoding these thermostable GGBPs.

10 Claims, 3 Drawing Sheets

SEQUENCE LISTING

<160> NUMBER OF SEQ ID NOS: 27

<210> SEQ ID NO 1
<211> LENGTH: 309
<212> TYPE: PRT
<213> ORGANISM: Escherichia coli

```
<400> SEQUENCE: 1

Ala Asp Thr Arg Ile Gly Val Thr Ile Tyr Lys Tyr Asp Asp Asn Phe
 1               5                  10                  15

Met Ser Val Val Arg Lys Ala Ile Glu Gln Asp Ala Lys Ala Ala Pro
             20                  25                  30

Asp Val Gln Leu Leu Met Asn Asp Ser Gln Asn Asp Gln Ser Lys Gln
         35                  40                  45

Asn Asp Gln Ile Asp Val Leu Leu Ala Lys Gly Val Lys Ala Leu Ala
     50                  55                  60

Ile Asn Leu Val Asp Pro Ala Ala Gly Thr Val Ile Glu Lys Ala
 65                  70                  75                  80

Arg Gly Gln Asn Val Pro Val Phe Phe Asn Lys Glu Pro Ser Arg
                 85                  90                  95

Lys Ala Leu Asp Ser Tyr Asp Lys Ala Tyr Tyr Val Gly Thr Asp Ser
                100                 105                 110

Lys Glu Ser Gly Ile Ile Gln Gly Asp Leu Ile Ala Lys His Trp Ala
                115                 120                 125

Ala Asn Gln Gly Trp Asp Leu Asn Lys Asp Gly Gln Ile Gln Phe Val
            130                 135                 140

Leu Leu Lys Gly Glu Pro Gly His Pro Asp Ala Glu Ala Arg Thr Thr
145                 150                 155                 160

Tyr Val Ile Lys Glu Leu Asn Asp Lys Gly Ile Lys Thr Glu Gln Leu
                165                 170                 175

Gln Leu Asp Thr Ala Met Trp Asp Thr Ala Gln Ala Lys Asp Lys Met
            180                 185                 190

Asp Ala Trp Leu Ser Gly Pro Asn Ala Asn Lys Ile Glu Val Val Ile
        195                 200                 205

Ala Asn Asn Asp Ala Met Ala Met Gly Ala Val Glu Ala Leu Lys Ala
    210                 215                 220

His Asn Lys Ser Ser Ile Pro Val Phe Gly Val Asp Ala Leu Pro Glu
225                 230                 235                 240

Ala Leu Ala Leu Val Lys Ser Gly Ala Leu Ala Gly Thr Val Leu Asn
                245                 250                 255

Asp Ala Asn Asn Gln Ala Lys Ala Thr Phe Asp Leu Ala Lys Asn Leu
            260                 265                 270

Ala Asp Gly Lys Gly Ala Ala Asp Gly Thr Asn Trp Lys Ile Asp Asn
        275                 280                 285

Lys Val Val Arg Val Pro Tyr Val Gly Val Asp Lys Asp Asn Leu Ala
    290                 295                 300

Glu Phe Ser Lys Lys
305

<210> SEQ ID NO 2
<211> LENGTH: 332
<212> TYPE: PRT
<213> ORGANISM: Escherichia coli

<400> SEQUENCE: 2

Met Asn Lys Lys Val Leu Thr Leu Ser Ala Val Met Ala Ser Met Leu
 1               5                  10                  15

Phe Gly Ala Ala Ala His Ala Ala Asp Thr Arg Ile Gly Val Thr Ile
             20                  25                  30

Tyr Lys Tyr Asp Asp Asn Phe Met Ser Val Val Arg Lys Ala Ile Glu
         35                  40                  45
```

```
Gln Asp Ala Lys Ala Ala Pro Asp Val Gln Leu Leu Met Asn Asp Ser
 50                  55                  60

Gln Asn Asp Gln Ser Lys Gln Asn Asp Gln Ile Asp Val Leu Leu Ala
 65                  70                  75                  80

Lys Gly Val Lys Ala Leu Ala Ile Asn Leu Val Asp Pro Ala Ala Ala
                 85                  90                  95

Gly Thr Val Ile Glu Lys Ala Arg Gly Gln Asn Val Pro Val Val Phe
            100                 105                 110

Phe Asn Lys Glu Pro Ser Arg Lys Ala Leu Asp Ser Tyr Asp Lys Ala
        115                 120                 125

Tyr Tyr Val Gly Thr Asp Ser Lys Glu Ser Gly Ile Ile Gln Gly Asp
130                 135                 140

Leu Ile Ala Lys His Trp Ala Ala Asn Gln Gly Trp Asp Leu Asn Lys
145                 150                 155                 160

Asp Gly Gln Ile Gln Phe Val Leu Leu Lys Gly Glu Pro Gly His Pro
                165                 170                 175

Asp Ala Glu Ala Arg Thr Thr Tyr Val Ile Lys Glu Leu Asn Asp Lys
            180                 185                 190

Gly Ile Lys Thr Glu Gln Leu Gln Leu Asp Thr Ala Met Trp Asp Thr
        195                 200                 205

Ala Gln Ala Lys Asp Lys Met Asp Ala Trp Leu Ser Gly Pro Asn Ala
210                 215                 220

Asn Lys Ile Glu Val Val Ile Ala Asn Asn Asp Ala Met Ala Met Gly
225                 230                 235                 240

Ala Val Glu Ala Leu Lys Ala His Asn Lys Ser Ser Ile Pro Val Phe
                245                 250                 255

Gly Val Asp Ala Leu Pro Glu Ala Leu Ala Leu Val Lys Ser Gly Ala
            260                 265                 270

Leu Ala Gly Thr Val Leu Asn Asp Ala Asn Asn Gln Ala Lys Ala Thr
        275                 280                 285

Phe Asp Leu Ala Lys Asn Leu Ala Asp Gly Lys Gly Ala Ala Asp Gly
290                 295                 300

Thr Asn Trp Lys Ile Asp Asn Lys Val Val Arg Val Pro Tyr Val Gly
305                 310                 315                 320

Val Asp Lys Asp Asn Leu Ala Glu Phe Ser Lys Lys
                325                 330

<210> SEQ ID NO 3
<211> LENGTH: 309
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 3

Ala Asp Thr Arg Ile Gly Val Thr Ile Tyr Lys Tyr Asp Asp Asn Phe
 1               5                  10                  15

Met Ser Val Val Arg Lys Ala Ile Glu Gln Asp Ala Lys Ala Ala Pro
                 20                  25                  30

Asp Val Gln Leu Leu Met Asn Asp Ser Gln Asn Asp Gln Ser Lys Gln
            35                  40                  45

Asn Asp Gln Ile Asp Val Leu Leu Ala Lys Gly Val Lys Ala Leu Ala
        50                  55                  60

Ile Asn Leu Val Asp Pro Ala Ala Ala Gly Thr Val Ile Glu Lys Ala
65                  70                  75                  80
```

Arg Gly Gln Asn Val Pro Val Val Phe Phe Asn Lys Glu Pro Ser Arg
            85                  90                  95

Lys Ala Leu Asp Ser Tyr Asp Lys Ala Tyr Tyr Val Gly Thr Asp Ser
            100                 105                 110

Lys Glu Ser Gly Ile Ile Gln Gly Asp Leu Ile Ala Lys His Trp Ala
            115                 120                 125

Ala Asn Gln Gly Trp Asp Leu Asn Lys Asp Gly Gln Ile Gln Phe Val
            130                 135                 140

Leu Leu Lys Gly Cys Pro Gly His Pro Asp Ala Glu Ala Arg Thr Thr
145                 150                 155                 160

Tyr Val Ile Lys Glu Leu Asn Asp Lys Gly Ile Lys Thr Glu Gln Leu
                165                 170                 175

Gln Leu Asp Thr Ala Met Trp Asp Thr Ala Gln Ala Lys Asp Lys Met
            180                 185                 190

Asp Ala Trp Leu Ser Gly Pro Asn Ala Asn Lys Ile Glu Val Val Ile
            195                 200                 205

Ala Asn Asn Asp Arg Met Ala Met Gly Ala Val Glu Ala Leu Lys Ala
            210                 215                 220

His Asn Lys Ser Ser Ile Pro Val Phe Gly Val Asp Ala Ser Pro Glu
225                 230                 235                 240

Ala Leu Ala Leu Val Lys Ser Gly Ala Leu Ala Gly Thr Val Leu Asn
                245                 250                 255

Asp Ala Asn Asn Gln Ala Lys Ala Thr Phe Asp Leu Ala Lys Asn Leu
            260                 265                 270

Ala Asp Gly Lys Gly Ala Ala Asp Gly Thr Asn Trp Lys Ile Asp Asn
            275                 280                 285

Lys Val Val Arg Val Pro Tyr Val Gly Val Asp Lys Asp Asn Leu Ala
            290                 295                 300

Glu Phe Ser Lys Lys
305

<210> SEQ ID NO 4
<211> LENGTH: 309
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 4

Ala Asp Thr Arg Ile Gly Val Thr Ile Tyr Lys Tyr Asp Asp Asn Phe
1               5                   10                  15

Met Ser Val Val Arg Lys Ala Ile Glu Gln Asp Ala Lys Ala Ala Pro
            20                  25                  30

Asp Val Gln Leu Leu Met Asn Asp Ser Gln Asn Asp Gln Ser Lys Gln
            35                  40                  45

Asn Asp Gln Ile Asp Val Leu Leu Ala Lys Gly Val Lys Ala Leu Ala
            50                  55                  60

Ile Asn Leu Val Asp Pro Ala Ala Gly Thr Val Ile Glu Lys Ala
65                  70                  75                  80

Arg Gly Gln Asn Val Pro Val Val Phe Phe Asn Lys Glu Pro Ser Arg
            85                  90                  95

Lys Ala Leu Asp Ser Tyr Asp Lys Ala Tyr Tyr Val Gly Thr Asp Ser
            100                 105                 110

Lys Glu Ser Gly Ile Ile Gln Gly Asp Leu Ile Ala Lys His Trp Ala
            115                 120                 125

```
Ala Asn Gln Gly Trp Asp Leu Asn Lys Asp Gly Gln Ile Gln Phe Val
130                 135                 140

Leu Leu Lys Gly Glu Pro Gly His Pro Asp Ala Glu Ala Arg Thr Thr
145                 150                 155                 160

Tyr Val Ile Lys Glu Leu Asn Asp Lys Gly Ile Lys Thr Glu Gln Leu
                165                 170                 175

Gln Leu Asp Thr Ala Met Cys Asp Thr Ala Gln Ala Lys Asp Lys Met
            180                 185                 190

Asp Ala Trp Leu Ser Gly Pro Asn Ala Asn Lys Ile Glu Val Val Ile
        195                 200                 205

Ala Asn Asn Asp Ala Met Ala Met Gly Ala Val Glu Ala Leu Lys Ala
210                 215                 220

His Asn Lys Ser Ser Ile Pro Val Phe Gly Val Asp Ala Leu Pro Glu
225                 230                 235                 240

Ala Leu Ala Leu Val Lys Ser Gly Ala Leu Ala Gly Thr Val Leu Asn
                245                 250                 255

Asp Ala Asn Asn Gln Ala Lys Ala Thr Phe Asp Leu Ala Lys Asn Leu
            260                 265                 270

Ala Asp Gly Lys Gly Ala Ala Asp Gly Thr Asn Trp Lys Ile Asp Asn
        275                 280                 285

Lys Val Val Arg Val Pro Tyr Val Gly Val Asp Lys Asp Asn Leu Ala
    290                 295                 300

Glu Phe Ser Lys Lys
305

<210> SEQ ID NO 5
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Met Gly His Asn His Asn His Asn His Asn His Asn Gly Gly
 1               5                  10                  15

Asp Asp Asp Asp Lys
            20

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Lys Lys Lys Lys Lys Lys Glu Glu
 1               5                  10

<210> SEQ ID NO 7
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 7

Ala Ala Pro Asp Val Gln Leu Leu Met Asn Asp Ser Gln Asn Asp Gln
 1               5                  10                  15

Ser Lys

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Lys Met Asp Ala Trp Leu Ser Gly Pro Asn Ala Asn Lys
 1               5                  10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

His Trp Ala Ala Asn Gln Gly Trp Asp Leu Asn Lys
 1               5                  10

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Thr Phe Asp Leu Ala Lys Asn Leu Ala Asp Gly Lys
 1               5                  10

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Ala Ala Asp Gly Thr Asn Trp Lys
 1               5

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Tyr Asp Asp Asn Phe Met Ser Val Val Arg
 1               5                  10
```

```
<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Asn Asp Gln Ile Asp Val Leu Leu Ala Lys
  1               5                  10

<210> SEQ ID NO 14
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Ala Pro Asp Val Gln Leu Leu Met Ile Asp Ser Gln Asn Asp Gln
  1               5                  10                  15

Ser Lys

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Lys Met Asp Ala Trp Leu Ser Ser Ser Lys Ala Asn Lys
  1               5                  10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

His Trp Ala Ala Asp Gln Gly Trp Asp Leu Asn Lys
  1               5                  10

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Thr Phe Asp Leu Ala Tyr Ser Leu Ala Asp Gly Lys
  1               5                  10

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 18

Gly Ala Ala Asp Gly Thr Asp Leu Lys
 1               5

<210> SEQ ID NO 19
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Ala Pro Asp Val Gln Leu Leu Met Ile Asp Gly Gln Gly Asp Gln
 1               5                  10                  15

Ser Lys

<210> SEQ ID NO 20
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Ala Pro Asp Val Gln Leu Leu Met Ile Asp Ser Gln Ala Asp Gln
 1               5                  10                  15

Ser Lys

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asp Lys Met Asp Ala Trp Leu Ser Ser Gly Lys Ala Lys Asp
 1               5                  10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

His Trp Lys Ala Asp Pro Thr Leu Asp Leu Asn Lys
 1               5                  10

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Thr Phe Asp Phe Ser Arg Leu Leu Ala Asp Gly Lys
 1               5                  10
```

```
<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Thr Phe Glu Leu Ala Arg Leu Leu Ala Asp Gly Lys
 1               5                  10

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Ala Ala Asp Gly Thr Met Pro Lys
 1               5

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Phe Asp Asp Thr Phe Met Ser Val Val Arg
 1               5                  10

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Ile Glu Gln Val Asp Val Leu Leu Ala Lys
 1               5                  10
```

US 8,778,635 B2

THERMOSTABLE PROTEINS AND METHODS MAKING AND USING THEREOF

SEQUENCE LISTING INFORMATION

A computer readable text file, entitled "P-6981-SequenceListing.txt," created on or about Jul. 11, 2013 with a file size of about 18 kb contains the sequence listing for this application and is hereby incorporated by reference in its entirety.

BACKGROUND OF THE INVENTION

1. Field of the Invention

The present invention relates to functional, modified glucose-galactose binding proteins (GGBPs), that have a greater melting temperature ($T_m$) than a reference GGBP. The present invention also relates to nucleic acids encoding these thermostable GGBPs, as well as methods of using these thermostable GGBPs

2. Background of the Invention

A rapidly advancing area of biosensor development is the use of periplasmic binding proteins (PBPs), to accurately determine analyte, e.g., glucose, concentrations in biological samples. In particular, glucose-galactose binding proteins (GGBPs) are being employed as biosensors to measure analyte quantities in industrial and pharmacological physiological settings. PBPs are considered to be "reagentless" and can be used in a variety of settings including measuring glucose in monitoring diabetes, measuring amino acids in other metabolic diseases, such as histidase deficiency, as well as measuring arabinose during ethanol production from corn. Wild-type GGBPs, however, may not be the most ideal candidates for measuring or determining analyte concentrations for a variety of reasons. Biosensors comprising GGBPs would preferably be physically stable under conditions of use to generate a quantifiable signal on glucose binding. When the intended use is monitor in vivo glucose concentrations in diabetics the proteins would preferably be stable at physiological temperatures. Additionally, the GGBPs would preferably have enhanced stability for sensor manufacturing, shipping and storage, which could potentially streamline and enable the protein and sensor materials to be fabricated at ambient temperature. This manufacturing process could include high-temperature sterilization procedures for use in a clinical setting. Exposure to high temperatures, however, may denature the protein, rendering the GGBPs useless for their intended purpose. Thus there is a need for GGBPs that are able to withstand higher temperatures while remaining active such that they can bind analyte and be used in biosensors in a variety of higher temperature settings.

SUMMARY OF THE INVENTION

The present invention relates to functional, modified glucose-galactose binding proteins (GGBPs), that have a greater melting temperature ($T_m$) than a reference GGBP.

The present invention also relates to nucleic acids encoding thermostable GGBPs.

The present invention also relates to functional, modified GGBPs, where the functional, modified GGBP has a greater melting temperature than a reference GGBP and where the modified GGBP further comprises at least one label.

BRIEF DESCRIPTION OF THE SEQUENCES IN THE SEQUENCE LISTING

SEQ ID NO:1 is the amino acid sequence of wild-type (*E. coli*) GGBP (GenBank Accession No. 2 GBP).

SEQ ID NO:2 is the amino acid sequence of wild-type (*E. coli*) GGBP GenBank Accession No. P0AEE5).

SEQ ID NO:3 is the amino acid sequence of 3M-GGBP, which has the following residue substitutions as compared to wild-type GGBP (SEQ ID NO:1): E149C, A213R, and L238S.

SEQ ID NO:4 is the amino acid sequence of W183C-GGBP, which has a W183C residue substitution as compared to wild-type GGBP.

SEQ ID NO:5 is the amino acid sequence of an amino acid tag, useful for peptide purification, that can be added to the N-terminus of a polypeptide of interest.

SEQ ID NO:6 is the amino acid sequence of an amino acid tag, useful for peptide purification and protein conjugation, that can be added to the C'-terminus of a polypeptide of interest.

DETAILED DESCRIPTION OF THE INVENTION

Figure 1:
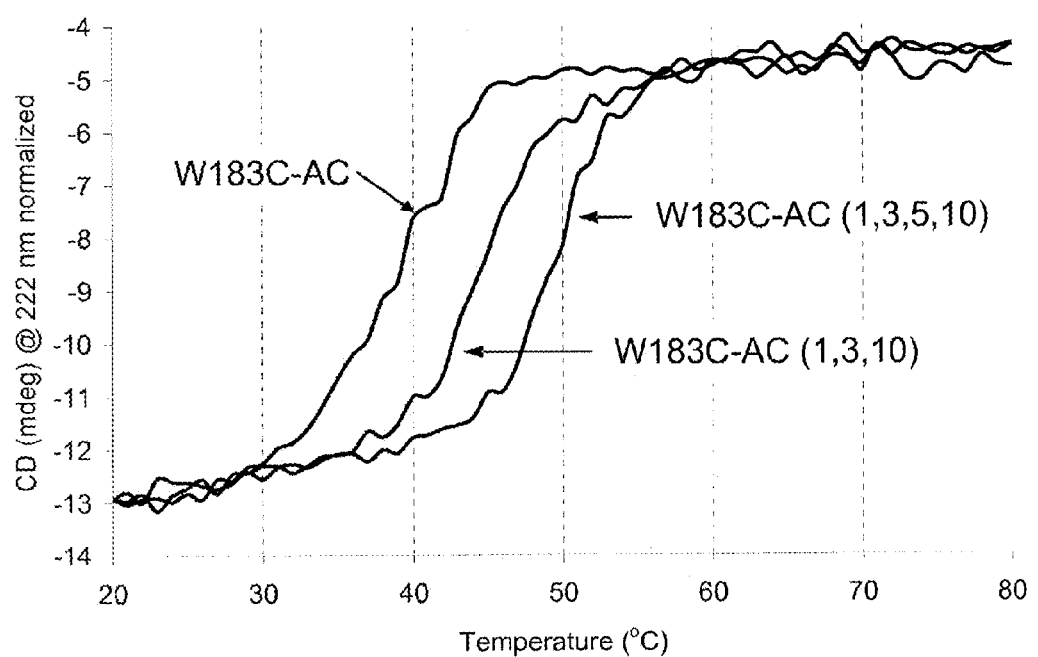
FIG. 1 depicts the thermal stability curves of a reference GGBP protein and two modified thermostable GGBPs.

The present invention relates to functional, modified periplasmic binding proteins (GGBPs), that have a greater melting temperature ($T_m$) than a reference GGBP.

Glucose-galactose binding protein is a member of the well-known class of periplasmic binding proteins, where these proteins are characterized by their three-dimensional configuration (tertiary structure), rather than the amino acid sequence (primary structure) of the protein. Each member of the class possesses a characteristic lobe-hinge-lobe motif See Dwyer, M. A. and Helling a, H. W., *Curr. Opin. Struct. Biol.*, 14:495-504 (2004), which is hereby incorporated by reference. The PBPs will normally bind an analyte specifically in a cleft region between the lobes of the PBP. Furthermore, the binding of an analyte in the cleft region will then cause a conformational change to the PBP that makes detection of the analyte possible. In general, the conformational changes to the PBP upon specific analyte binding are characterized by the two lobe regions to bend towards each other around and through the hinge region. See Quiocho, F. A. and Ledvina, P. S., *Mol. Microbiol.* 20:17-25 (1996), which is incorporated by reference. Examples of PBPs include, but are not limited to, glucose-galactose binding protein (GGBP), maltose binding protein (MBP), ribose binding protein (RBP), arabinose binding protein (ABP), dipeptide binding protein (DPBP), glutamate binding protein (GluBP), iron binding protein (FeBP), histidine binding protein (HBP), phosphate binding protein (PhosBP), glutamine binding protein (QBP), leucine binding protein (LBP), leucine- isoleucine- valine-binding protein (LIVBP), oligopeptide binding protein (OppA), or derivatives thereof, as well as other proteins that belong to the families of proteins known as periplasmic binding protein like I (PBP-like I) and periplasmic binding protein like II (PBP-like II).

For the purposes of the present invention, a glucose-galactose binding protein (GGBP) includes any protein that possesses these structural characteristics described herein and can specifically bind to glucose and/or galactose.

In particular, the invention relates to modified of GGBPs. A "modified protein" is used to mean a protein can be created by addition, deletion or substitution of one or more amino acids in the primary structure (amino acid sequence) of a reference protein or polypeptide. The terms "protein" and "polypeptide" are used interchangeably herein. The reference protein need not be a wild-type protein, but can be any protein that is targeted for modification for the purposes of increasing thermal stability. Thus, the reference protein may be a protein whose sequence was previously modified over a wild-type protein. Of course, the reference protein may or may not be the wild-type protein from a particular organism. Furthermore, the term "wild-type protein" includes the wild-type protein with or without a "leader sequence."

The modified GGBPs of the present the invention are functional and thermostable. As used herein, a functional, modified GGBP is capable of specifically binding an analyte of interest. In particular the binding of the analyte to the modified GGBP should cause the characteristic "ligand-mediated hinge-bending motions" similar to what is observed when a wild-type GGBP binds the analyte, i.e., the bending of the two lobe regions towards each other through the hinge region. Dwyer, M. A. and Helling a, H. W., *Curr. Opin. Struct. Biol.*, 14:495-504 (2004). The degree of movement of the lobe regions, however, need not be the same as in the wild-type GGBP.

Figure 3:
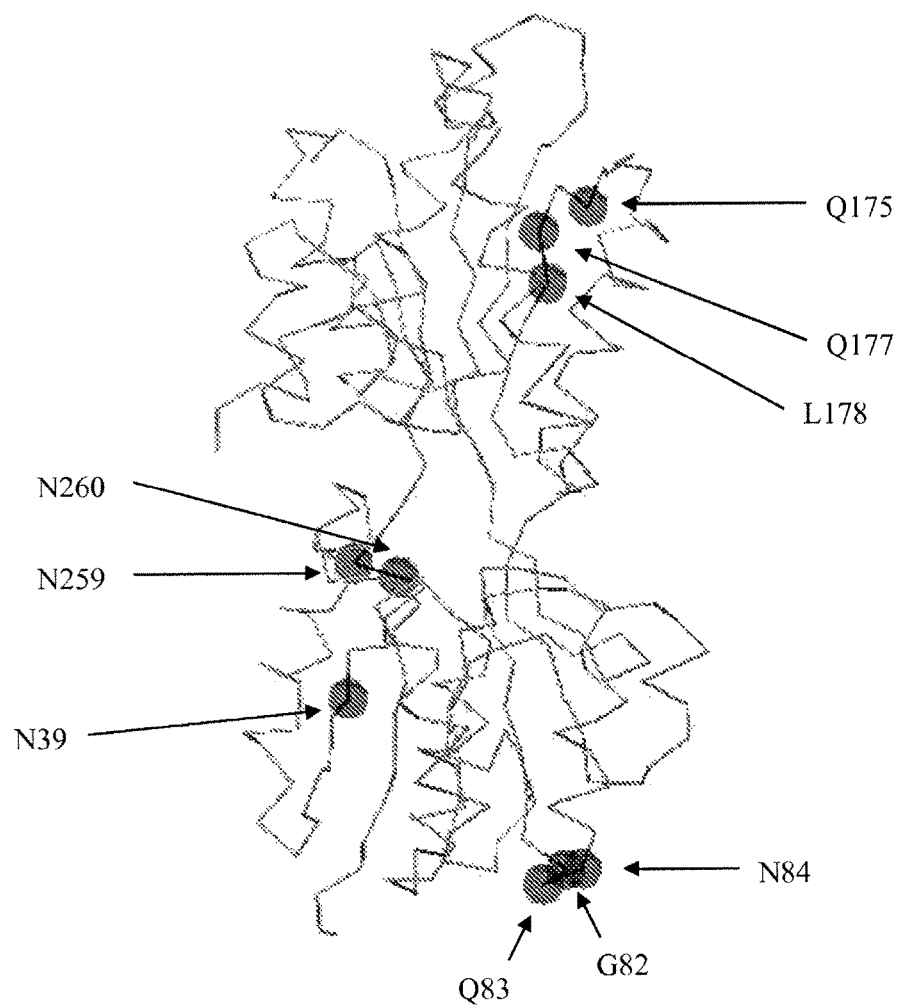
FIG. 3 depicts representative amino acids that may be targeted for substitution.

In one example, the modified polypeptide of the invention can be a modified GGBP, where "surface" amino acids in the reference protein have been mutated. The phrase "surface amino acids" of a protein is used as it is in the art and is used to mean, in general, the residues of a folded protein that may be exposed to solvent or other environment. One specific embodiment of the present invention, therefore, relates to modified GGBPs where one or more surface residues of the reference GGBP have been mutated. In particular, surface asparagine residues and surface glutamine residues may be targeted for substitution. For example, asparagine residues corresponding to, for example, positions asparagine 39 (N39), asparagine 84 (N84), asparagine 130 (N130), asparagine 200 (N200), asparagine 226 (N226), asparagine 259 (N259), asparagine 260 (N260), asparagine 271 (N271), asparagine 283 (N283), and asparagine 302 (N302) of SEQ ID NO: 1 may be targeted for substitution. Similarly, in addition to or in the alternative, glutamine residues corresponding to, for example, positions glutamine 51 (Q51), glutamine 83 (Q83), glutamine 175 (Q175), glutamine 177 (Q177) and leucine 178 (L178) of SEQ ID NO: 1, may also be targeted for substitution. Examples of surface amino acids that may be targeted for modification include, but are not limited to those residues illustrated in FIG. 3. Other surface residues may also be selected for substitution based upon, for example, NCBI's molecular modeling database (MMDB) accession record number 2GBP (available on the World Wide Web at ncbi.nlm.nih.gov/entrez/query.fcgi). Thus, one specific embodiment of the present invention relates to a modified GGBP, where at least one surface glutamine amino acid in the reference GGBP has been mutated. Another specific embodiment of the present invention relates to a modified GGBP, where at least one surface asparagine amino acid in the reference GGBP has been mutated. And yet another specific embodiment of the present invention relates to a modified GGBP, where at least one surface glutamine amino acid and one surface asparagine amino acid in the reference GGBP has been mutated. Of course, the modified GGBPs of the present invention may comprise additional modification, and the modifications need not be targeted against solely surface asparagines or glutamines.

In additional embodiments, amino acids are targeted for mutation based upon the deamidation or potential deamidation of residues in a peptide or protein. As one of skill in the art is aware, deamidation is a chemical reaction wherein an amide group is altered. In relation to peptides, deamidation can potentially degrade or destroy the functionality of the protein or peptide that contains amide-containing amino acids. Examples of amide-containing amino acids include, but are not limited to asparagine and glutamine. Deamidation, in general, will occur more rapidly with increased temperature and pH. The process of deamidation thus makes peptides and proteins susceptible to heat inactivation. See Xie, M. and Schowen, R. L., *J. Pharm. Sci.*, 88(1):8-13 (1999), which is incorporated by reference. In one embodiment, therefore, deamidation-prone amino acids are targeted for substitution or deletion. The methods used to determine deamidation-prone amino acids should not limit the scope of the present invention. In one specific embodiment, Fourier transform mass spectroscopy (FTMS) may be used to measure relative deamidation at susceptible residues such as asparagine residues.

As used herein, the terms "correspond(s) to" and "corresponding to," as they relate to sequence alignment, are intended to mean enumerated positions within the reference protein, e.g., wild-type *E. coli* GGBP, and those positions in the modified GGBP that align with the positions on the reference protein. Thus, when the amino acid sequence of a subject GGBP is aligned with the amino acid sequence of a reference GGBP, e.g., SEQ ID NO:1, the amino acids in the subject GGBP sequence that "correspond to" certain enumerated positions of the reference GGBP sequence are those that align with these positions of the reference GGBP sequence, but are not necessarily in these exact numerical positions of the reference GGBP sequence. Methods for aligning sequences for determining corresponding amino acids between sequences are described below.

In one embodiment of the present invention, the modified GGBP is a modified wild-type GGBP from *E. coli*. Thus, in this embodiment, the reference protein for the modified GGBP is wild-type GGBP that comprises the amino acid sequence of SEQ ID NO:1, below, and accessible in the database for The National Center for Biotechnology Information (NCBI) as GenBank Accession No. 2 GBP, the entire record of which is incorporated by reference. The NCBI GenBank database is found on the world-wide web at www.ncbi.nih.gov/Genbank.

(SEQ ID NO: 1)

```
  1 ADTRIGVTIY KYDDNFMSVV RKAIEQDAKA APDVQLLMND SQNDQSKQND QIDVLLAKGV

61 KALAINLVDP AAAGTVIEKA RGQNVPVVFF NKEPSRKALD SYDKAYYVGT DSKESGIIQG

121 DLIAKHWAAN QGWDLNKDGQ IQFVLLKGEP GHPDAEARTT YVIKELNDKG IKTEQLQLDT

181 AMWDTAQAKD KMDAWLSGPN ANKIEVVIAN NDAMAMGAVE ALKAHNKSSI PVFGVDALPE

241 ALALVKSGAL AGTVLNDANN QAKATFDLAK NLADGKGAAD GTNWKIDNKV VRVPYVGVDK

301 DNLAEFSKK
```

In particular embodiments, the modified GGBP comprises one or more residue substitutions at positions corresponding to one or more of the following residues of SEQ ID NO:1: tyrosine 12 (Y12), asparagine 15 (N15), asparagine 39 (N39), serine 41 (S41), asparagine 43 (N43), asparagine 49 (N49), aspartic acid 50 (D50), glutamine 51 (Q51), isoleucine 52 (I52), glycine 82 (G82), glutamine 83 (Q83), asparagine 84 (N84), alanine 128 (A128), alanine 129 (A129), asparagine 130 (N130), glutamine 131 (Q131), glycine 132 (G132), tryptophan 133 (W133), glutamine 175 (Q175), glutamine 177 (Q177), leucine 178 (L178), glycine 198 (G198), proline 199 (P199), asparagine 200 (N200), asparagine 202 (N202), lysine 203 (K203) asparagine 226 (N226), asparagine 259 (N259), asparagine 260 (N260), aspartic acid 267 (D267), alanine 269 (A269), lysine 270 (K270), asparagine 271 (N271), asparagine 283 (N283), tryptophan 284 (W284) and asparagine 302 (N302).

In another embodiment of the present invention, the modified GGBP is a modified wild-type GGBP from *E. coli*, where the wild-type GGBP possesses its native leader sequence. Thus, in this embodiment, the reference protein for the modified GGBP comprises the amino acid sequence of SEQ ID NO:2, below, and accessible as GenBank Accession No. P02927 the entire record of which is incorporated by reference.

(SEQ ID NO: 2)
```
  1 MNKKVLTLSA VMASMLFGAA AHAADTRIGV TIYKYDDNFM SVVRKAIEQD AKAAPDVQLL

61 MNDSQNDQSK QNDQIDVLLA KGVKALAINL VDPAAAGTVI EKARGQNVPV VFFNKEPSRK

121 ALDSYDKAYY VGTDSKESGI IQGDLIAKHW AANQGWDLNK DGQIQFVLLK GEPGHPDAEA

181 RTTYVIKELN DKGIKTEQLQ LDTAMWDTAQ AKDKMDAWLS GPNANKIEVV IANNDAMAMG

241 AVEALKAHNK SSIPVFGVDA LPEALALVKS GALAGTVLND ANNQAKATFD LAKNLADGKG

301 AADGTNWKID NKVVRVPYVG VDKDNLAEFS KK
```

In particular embodiments, the modified GGBP comprises one or more residue substitutions at positions corresponding to one or more of the following residues of SEQ ID NO:2: tyrosine 35 (Y35), asparagine 38 (N38), asparagine 62 (N62), serine 64 (S64), asparagine 66 (N66), asparagine 72 (N72), aspartic acid 73 (D73), glutamine 74 (Q74), isoleucine 75 (I75), glycine 105 (G105), glutamine 106 (Q106), asparagine 107 (N107), alanine 151 (A151), alanine 152 (A152), asparagine 153 (N153), glutamine 154 (Q154), glycine 155 (G155), tryptophan 156 (W156), glutamine 198 (Q198), glutamine 200 (Q200), leucine 201 (L201), glycine 221 (G221), proline 222 (P222), asparagine 223 (N223), asparagine 202 (N225), lysine 226 (K226) asparagine 249 (N249), asparagine 282 (N282), asparagine 283 (N283), aspartic acid 290 (D290), alanine 292 (A292), lysine 293 (K293), asparagine 294 (N294), asparagine 306 (N306), tryptophan 307 (W307) and asparagine 325 (N302).

In another embodiment of the present invention, the modified GGBP is a further modification a previously modified GGBP having 3 amino acid substitutions as compared to the wild-type (*E. coli*) GGBP, which is termed "3M-GGBP." The construction of 3M-GGBP, which has substitutions corresponding to E149C, A213R L238S, as compared to SEQ ID NO:1, is described in U.S. Pat. No. 6,855,556, which is incorporated by reference. Thus, in this embodiment, the reference protein for the modified GGBP is 3M-GGBP that comprises the amino acid sequence of SEQ ID NO:3, below.

(SEQ ID NO: 3)
```
  1 ADTRIGVTIY KYDDNFMSVV RKAIEQDAKA APDVQLLMND SQNDQSKQND

51 QIDVLLAKGV KALAINLVDP AAAGTVIEKA RGQNVPVVFF NKEPSRKALD

101 SYDKAYYVGT DSKESGIIQG DLIAKHWAAN QGWDLNKDGQ IQFVLLKGCP

151 GHPDAEARTT YVIKELNDKG IKTEQLQLDT AMWDTAQAKD KMDAWLSGPN

201 ANKIEVVIAN NDRMAMGAVE ALKAHNKSSI PVFGVDASPE ALALVKSGAL

251 AGTVLNDANN QAKATFDLAK NLADGKGAAD GTNWKIDNKV VRVPYVGVDK

301 DNLAEFSKK
```

In particular embodiments, the modified GGBP comprises one or more residue substitutions at positions corresponding to one or more of the following residues of SEQ ID NO:3: tyrosine 12 (Y12), asparagine 15 (N15), asparagine 39 (N39), serine 41 (S41), asparagine (N43), asparagine 49 (N49), aspartic acid 50 (D50), glutamine 51 (Q51), isoleucine (I52), glycine 82 (G82), glutamine 83 (Q83), asparagine 84 (N84), alanine 128 (A128), alanine 129 (A129), asparagine 130 (N130), glutamine (Q131), glycine 132 (G132), tryptophan 133 (W133), glutamine 175 (Q175), glutamine 177 (Q177), leucine 178 (L178), glycine 198 (G198), proline 199 (P199), asparagine 200 (N200), asparagine (N202), lysine (K203) asparagine 226 (N226), asparagine 259 (N259), asparagine 260 (N260), aspartic acid 267 (D267), alanine 269 (A269), lysine 270 (K270), asparagine 271 (N271), asparagine 283 (N283), tryptophan 284 (W284) and asparagine 302 (N302).

In another embodiment of the present invention, the modified GGBP is a further modification a previously modified GGBP having a single amino acid substitution of tryptophan 183 to cysteine (W183C) as compared to the wild-type (*E. coli*) GGBP, which is termed "W183C-GGBP" or "W183." Thus, in this embodiment, the reference protein for the modified GGBP is W183C-GGBP that comprises the amino acid sequence of SEQ ID NO:4, below.

substituting more than one amino acid centered on position 83 of the reference GGBP, i.e., glutamic acid, lysine and aspartic acid may be substituted for positions 82-84 respectively in a substitution targeting the single glutamine at position 83.

The invention also contemplates modified GGBPs wherein the reference proteins for the modified GGBPs comprise an amino acid sequence at least about 80% identical to the amino acid sequence of SEQ ID NO:1, 2, 3 or 4. In specific embodiments, the polypeptides of the present invention are at least about 85%, 90%, 95%, 96%, 97%, 98% and 99% identical to the amino acid sequence of SEQ ID NO:1, 2, 3 or 4. In other embodiments, the reference GGBP could be wild-type GGBPs from species other than *E. coli*, including but not limited to, *Clostridium, acetobutylicum, S. solfataricus, A. tumefaciens, Rhodobacter capsulatus, Neisseria gonorrhoeae, Y. enterocolitica, Haemophilus influenzae, Klebsiella oxytoca, B. Subtilis, Salmonella typhimurium, S. typhimurium, Treponema pallidum.*

A polypeptide having an amino acid sequence at least, for example, about 95% "identical" to a reference an amino acid sequence encoding GGBP is understood to mean that the amino acid sequence of the polypeptide is identical to the reference sequence except that the amino acid sequence may

```
                                                              (SEQ ID NO: 4)
  1 ADTRIGVTIY KYDDNFMSVV RKAIEQDAKA APDVQLLMND SQNDQSKQND

51 QIDVLLAKGV KALAINLVDP AAAGTVIEKA RGQNVPVVFF NKEPSRKALD

101 SYDKAYYVGT DSKESGIIQG DLIAKHWAAN QGWDLNKDGQ IQFVLLKGEP

151 GHPDAEARTT YVIKELNDKG IKTEQLQLDT AMCDTAQAKD KMDAWLSGPN

201 ANKIEVVIAN NDAMAMGAVE ALKAHNKSSI PVFGVDALPE ALALVKSGAL

251 AGTVLNDANN QAKATFDLAK NLADGKGAAD GTNWKIDNKV VRVPYVGVDK

301 DNLAEFSKK
```

In particular embodiments, the modified GGBP comprises one or more residue substitutions at positions corresponding to one or more of the following residues of SEQ ID NO:4: tyrosine 12 (Y12), asparagine 15 (N15), asparagine 39 (N39), serine 41 (S41), asparagine (N43), asparagine 49 (N49), aspartic acid 50 (D50), glutamine 51 (Q51), isoleucine (I52), glycine 82 (G82), glutamine 83 (Q83), asparagine 84 (N84), alanine 128 (A128), alanine 129 (A129), asparagine 130 (N130), glutamine (Q131), glycine 132 (G132), tryptophan 133 (W133), glutamine 175 (Q175), glutamine 177 (Q177), leucine 178 (L178), glycine 198 (G198), proline 199 (P199), asparagine 200 (N200), asparagine (N202), lysine (K203) asparagine 226 (N226), asparagine 259 (N259), asparagine 260 (N260), aspartic acid 267 (D267), alanine 269 (A269), lysine 270 (K270), asparagine 271 (N271), asparagine 283 (N283), tryptophan 284 (W284) and asparagine 302 (N302).

In some embodiments, each amino acid targeted for modification on the wild-type or reference protein is modified by substituting a single amino acid at the targeted site, such that the one or more substitution occurs in a 1-to-1 fashion. For example, an asparagine at position 39 of wild-type *E. coli* GGBP (SEQ ID NO:1) may be modified by substituting a different amino acid, e.g., isoleucine or valine. In other embodiments, more than one amino acid is substituted at and flanking (but not necessarily directly adjacent to) the targeted site, such that a "locus" on the wild-type or reference protein is mutated. For example, a glutamine at position 83 of wild-type *E. coli* GGBP (SEQ ID NO:1) may be modified by include up to about five modifications per each 100 amino acids of the reference amino acid sequence encoding the reference GGBP. In other words, to obtain a peptide having an amino acid sequence at least about 95% identical to a reference amino acid sequence, up to about 5% of the amino acid residues of the reference sequence may be deleted or substituted with another amino acid or a number of amino acids up to about 5% of the total amino acids in the reference sequence may be inserted into the reference sequence. These modifications of the reference sequence may occur at the N-terminus or C-terminus positions of the reference amino acid sequence or anywhere between those terminal positions, interspersed either individually among amino acids in the reference sequence or in one or more contiguous groups within the reference sequence.

As used herein, "identity" is a measure of the identity of nucleotide sequences or amino acid sequences compared to a reference nucleotide or amino acid sequence. In general, the sequences are aligned so that the highest order match is obtained. "Identity" per se has an art-recognized meaning and can be calculated using published techniques. (See, e.g., Computational Molecular Biology, Lesk, A. M., ed., Oxford University Press, New York (1988); Biocomputing: Informatics And Genome Projects, Smith, D. W., ed., Academic Press, New York (1993); Computer Analysis of Sequence Data, Part I, Griffin, A. M., and Griffin, H. G., eds., Humana Press, New Jersey (1994); von Heinje, G., Sequence Analysis In Molecular Biology, Academic Press (1987); and Sequence Analysis Primer, Gribskov, M. and Devereux, J., eds., M Stockton Press, New York (1991)). While there exist several methods to measure identity between two polynucleotide or polypeptide sequences, the term "identity" is well known to skilled artisans (Carillo, H. & Lipton, D., Siam J Applied Math 48:1073 (1988)). Methods commonly employed to determine identity or similarity between two sequences include, but are not limited to, those disclosed in Guide to Huge Computers, Martin J. Bishop, ed., Academic Press, San Diego (1994) and Carillo, H. & Lipton, D., Siam J Applied Math 48:1073 (1988). Computer programs may also contain methods and algorithms that calculate identity and similarity. Examples of computer program methods to determine identity and similarity between two sequences include, but are not limited to, GCG program package (Devereux, J., et al., Nucleic Acids Research 12(i):387 (1984)), BLASTP, ExPASy, BLASTN, FASTA (Atschul, S. F., et al., J Molec Biol 215:403 (1990)) and FASTDB. Examples of methods to determine identity and similarity are discussed in Michaels, G. and Garian, R., *Current Protocols in Protein Science*, Vol 1, John Wiley & Sons, Inc. (2000), which is incorporated by reference. In one embodiment of the present invention, the algorithm used to determine identity between two or more polypeptides is BLASTP.

In another embodiment of the present invention, the algorithm used to determine identity between two or more polypeptides is FASTDB, which is based upon the algorithm of Brutlag et al. (Comp. App. Biosci. 6:237-245 (1990), incorporated by reference). In a FASTDB sequence alignment, the query and subject sequences are amino sequences. The result of sequence alignment is in percent identity. Parameters that may be used in a FASTDB alignment of amino acid sequences to calculate percent identity include, but are not limited to: Matrix=PAM, k-tuple=2, Mismatch Penalty=1, Joining Penalty=20, Randomization Group Length=0, Cutoff Score=1, Gap Penalty=5, Gap Size Penalty 0.05, Window Size=500 or the length of the subject amino sequence, whichever is shorter.

If the subject sequence is shorter or longer than the query sequence because of N-terminus or C-terminus additions or deletions, not because of internal additions or deletions, a manual correction can be made, because the FASTDB program does not account for N-terminus and C-terminus truncations or additions of the subject sequence when calculating percent identity. For subject sequences truncated at the 5' or 3' ends, relative to the query sequence, the percent identity is corrected by calculating the number of bases of the query sequence that are N- and C-terminus to the reference sequence that are not matched/aligned, as a percent of the total bases of the query sequence. The results of the FASTDB sequence alignment determine matching/alignment. The alignment percentage is then subtracted from the percent identity, calculated by the above FASTDB program using the specified parameters, to arrive at a final percent identity score. This corrected score can be used for the purposes of determining how alignments "correspond" to each other, as well as percentage identity. Residues of the query (subject) sequences or the reference sequence that extend past the N- or C-termini of the reference or subject sequence, respectively, may be considered for the purposes of manually adjusting the percent identity score. That is, residues that are not matched/aligned with the N- or C-termini of the comparison sequence may be counted when manually adjusting the percent identity score or alignment numbering.

For example, a 90 amino acid residue subject sequence is aligned with a 100 residue reference sequence to determine percent identity. The deletion occurs at the N-terminus of the subject sequence and therefore, the FASTDB alignment does not show a match/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 reference sequence. This time the deletions are internal deletions so there are no residues at the N- or C-termini of the subject sequence which are not matched/aligned with the query. In this case the percent identity calculated by FASTDB is not manually corrected.

The modified GGBPs of the invention may have improved characteristics, such as increased stability (e.g., thermal stability, detergent stability, pH stability, freeze/thaw stability) or increased solubility in aqueous solvents, relative to the reference GGBP. In particular, the modified GGBPs of the present invention are thermostable or heat stable. The terms "thermostable" or "heat stable" are used interchangeably herein and are used to indicate that the modified GGBPs have a higher melting temperature than the reference GGBP from which the modified GGBPs have been derived. Melting temperature, as the term relates to proteins, is used herein as it is in the art. Namely, the melting temperature is the temperature at which the populations of folded and unfolded protein in a sample are equal. There are numerous methods for determining the melting temperature of a protein, and the invention should not be limited by the methods of determining the melting temperature of the proteins. Provided that the method for determining the melting temperature of the reference and modified proteins are the same, then a thermostable protein, for the purposes of the present invention, is a protein that has a higher melting temperature than the reference protein. One example of a method of measuring the melting temperature of a protein includes, but is not limited to, circular dichroism, which is a spectrophotometric method that differentially measures the absorption of right-handed and left-handed circularly-polarized light to monitor the three dimensional configuration of a protein. Methods of Circular Dichroism are discussed in Miles, A. J. and Wallace, B. A., *Chem. Soc. Rev.,* 35: 39-31 (2006), which is incorporated by reference.

In the instant invention, analyte and modified glucose-galactose binding protein act as binding partners. The term "associates" or "binds" as used herein refers to specific binding. Affinity of specific binding can be assessed by calculating a relative binding constant such as, but not limited to, equilibrium dissociation constant ($K_d$). The $K_d$ may be calculated as the concentration of free analyte at which half the binding molecule is bound, or vice versa. When the analyte of interest is glucose, for example, the $K_d$ values for the binding partners may be between about 0.0001 mM to about 30 mM. Accordingly, the modified glucose-galactose binding proteins of the present invention may be used in an in vitro or in vivo analyte assay which, for example, is capable of following the kinetics of biological reactions involving an analyte, such as glucose, as well as in clinical assays. A protein or modified protein with a greater dissociation constant than a reference protein means that the binding of the protein or modified protein to the target analyte is weaker, or that the binding affinity of the modified GGBP is decreased. Conversely, a protein or modified protein with a smaller dissociation constant than a reference protein means that the binding of the protein or modified protein to the target analyte is stronger, or that the binding affinity of the modified GGBP is increased. For example, a protein with a Kd of about 1 mM is considered to have a "weaker" binding affinity than a protein with a Kd of about 0.1 mM.

Thus, in one embodiment of the present invention, the binding affinity of the modified GGBP towards its analyte binding partner is substantially the same as the binding affinity of the wild-type GGBP towards the same analyte binding partner. As used herein, the term "substantially the same" as compared to the binding affinity indicates that the measured binding affinities of the modified GGBP and reference GGBP towards the analyte binding partner are within one order of magnitude of each other. For example if the metric used to determine and compare binding affinities is dissociation constant, then a protein with a Kd of about 1 mM is considered to have substantially the same binding affinity as a protein with a Kd of about 0.1 mM, even though one protein is measurably weaker than the other protein. To be clear, however, one protein may have a weaker binding affinity as compared to another protein, but the two proteins would still have "substantially the same" binding affinities for the purposes of the present invention.

In another embodiment, the binding affinity of the modified GGBP towards its binding partner is altered as compared to the binding affinity of the reference GGBP towards the same analyte binding partner. As used herein, a binding affinity is "altered" when the affinities of the modified GGBP and the reference GGBP towards the same analyte binding partner are not within one order of magnitude of each other. In one embodiment, the present invention relates to methods of decreasing the binding affinity of the modified GGBP towards its analyte binding partner as compared to the binding affinity of the reference GGBP towards the same analyte. In another embodiment, the present invention relates to methods of increasing the binding affinity of the modified GGBP towards its analyte binding partner as compared to the binding affinity of the reference GGBP towards the same analyte.

Likewise, one aspect of the present invention relates to methods of altering the affinity of the binding molecules towards their targets, while also increasing the thermal stability of the modified GGBP. In one embodiment, the present invention relates to methods of decreasing the binding affinity of the modified GGBP towards an analyte binding partner as compared to the binding affinity of the reference GGBP towards the same binding partner. In another embodiment, the present invention relates to methods of altering the selectivity of the modified GGBP as compared to the selectivity of the reference GGBP.

In another embodiment, the fluorescence response, relative, absolute or ratiometric, of the modified GGBP towards its binding partner is altered as compared to the fluorescence response which can be relative, absolute or ratiometric of the reference GGBP towards the same analyte binding partner. Methods of determining and measuring relative fluorescence are described in Lakowicz, J. R. (1999) *Principles of Fluorescence Spectroscopy*, Second Edition, pp 185-210, Kluwer Academic/Plenum Publishers, New York, which is incorporated by reference. Methods of determining and measuring ratiometric fluorescence are described in De Lorimier, R. M., Smith, J. J., Dwyer, M. A., Looger, L. L., Sali, K. M., Paavola, C. D., Rizk, S. S., Sadigov, S., Conrad, D. W., Loew, L., and Helling a, H. W. (2002) Construction of a fluorescent biosensor family. Protein *Sci.* 11, 2655-2675, which is incorporated by reference. As used herein, relative fluorescence response is "altered" when the fluorescence of the modified GGBP, upon binding of analyte, is beyond one order of magnitude of the fluorescence of the reference GGBP upon binding the same analyte. In one embodiment, the present invention relates to methods of decreasing the fluorescence of the modified GGBP towards its analyte binding partner as compared to the fluorescence of the reference GGBP towards the same analyte. In another embodiment, the present invention relates to methods of increasing the binding affinity of the modified GGBP towards its analyte binding partner as compared to the binding affinity of the reference GGBP towards the same analyte.

In another specific embodiment, the modified proteins may be modified to bind more than one analyte in a specific manner. Indeed, the modified proteins may possess specificity for the same ligand as the reference GGBP in addition to another target ligand.

Likewise, the modified proteins may be able to bind only one or more analytes that the reference binding protein does not bind. Methods of altering protein selectivity or specificity have been described. For example, Looger, et al., (*Nature* 423 (6936): 185-190 (2003)), which is hereby incorporated by reference, disclose methods for re-designing binding sites within periplasmic binding proteins that provide new analyte-binding properties for the proteins. These modified binding proteins retain the ability to undergo conformational change, which can produce a directly generated signal upon analyte-binding. By introducing between 5 and 17 amino acid changes, Looger, et al. constructed several modified proteins, each with new selectivities for TNT (trinitrotoluene), L-lactate, or serotonin. For example, Looger et al. generated L-lactate binding proteins from ABP, GGBP, RBP, HBP and QBP. In one embodiment, the device comprises a mutated thermostable GGBP that specifically binds L-lactate. In this embodiment, the reference GGBP would be the previously mutated GGBP there the binding specificity for glucose and galactose had been ablated and was now able to specifically bind L-lactate. This reference GGBP would then, for the purposes of the present invention, be mutated to increase the thermal stability of the modified, L-lactate-specific GGBP.

The modified thermostable GGBPs may but need not be labeled to detect or measure analyte in a sample. Examples of assays in which unlabeled, modified, thermostable GGBPs of the present invention include, but are not limited to, surface plasmon resonance (SPR) and surface enhanced Raman spectroscopy (SERS). In another embodiment, the reference GGBPs and the modified thermostable GGBPs may also comprise one or more labeling moieties. A "labeling moiety," as used herein, is intended to mean a chemical compound or ion that possesses or comes to possess a detectable signal. The labels used in the present invention may be used to indicate a conformational change in the lobe regions of the GGBPs. Examples of changes in lobe regions include, but are not limited to, three-dimensional conformational changes, changes in orientation of the amino acid side chains of proteinaceous binding domains, and redox states of the binding domains. With the addition/substitution of one or more residues into the primary structure of a protein, some of the labeling moieties used in the current methods and compositions can be attached through chemical means, such as reduction, oxidation, conjugation, and condensation reactions. Examples of residues commonly used to label proteins include, but are limited to, lysine and cysteine. For example, any thiol-reactive group can be used to attach labeling moieties, e.g., a fluorophore, to a naturally occurring or engineered cysteine in the primary structure of the polypeptide. U.S. Pat. No. 6,855,556, which is incorporated by reference, describes various cysteine mutations of PBPs. Also, for example, lysine residues can be labeled using succinimide ester derivatives of fluorophores. See Richieri, G. V. et al., *J. Biol. Chem.*, 267: 23495-501 (1992) which is hereby incorporated by reference.

The labeling moieties of the present invention may be radioactive or non-radioactive. Examples of radiolabels include, but are not limited to, $^3$H and $^{32}$P, that can be measured with radiation-counting devices. Examples of non-radioactive labels include, but are not limited to, transition metals, lanthanide ions and other chemical compounds. The non-radioactive signals include, but are not limited to, fluorescence, phosphorescence, bioluminescence, electrochemical and chemiluminescence pigments, dyes or other chromogens that can be visually observed or measured with a spectrophotometer; spin labels that can be measured with a spin label analyzer; and fluorescent labels (fluorophores), where the output signal is generated by the excitation of a suitable molecular adduct and that can be visualized by excitation with light that is absorbed by the dye or can be measured with standard fluorometers or imaging systems. Additional examples of labels include, but are not limited to, a phosphorescent dye, a tandem dye and a particle. The label can be a chemiluminescent substance, where the output signal is generated by chemical modification of the signal compound; a metal-containing substance; or an enzyme, whereby an enzyme-dependent secondary generation of signal is generated, such as the formation of a colored product from a colorless substrate. The term label also includes a "tag" or hapten that can bind selectively to a conjugated molecule such that the conjugated molecule, when added subsequently along with a substrate, is used to generate a detectable signal. For example, one can use biotin as a label and subsequently use an avidin or streptavidin conjugate of horseradish peroxidate (HRP) to bind to the biotin label and subsequently use a colorimetric substrate (e.g., tetramethylbenzidine (TMB)) or a fluorogenic substrate such as Amplex Red reagent (Molecular Probes, Inc.) to detect the presence of HRP. Numerous labels are known by those of skill in the art and include, but are not limited to, particles, fluorophores, haptens, enzymes and their colorimetric, fluorogenic and chemiluminescent substrates and other labels that are described in RICHARD P. HAUGLAND, MOLECULAR PROBES HANDBOOK OF FLUORESCENT PROBES AND RESEARCH PRODUCTS (9$^{th}$ edition, CD-ROM, (September 2002), which is herein incorporated by reference.

A fluorophore of the present invention is any chemical moiety that exhibits an absorption maximum at or beyond 280 nm, and when covalently attached to a protein or other reagent retains its spectral properties. Fluorophores of the present invention include, without limitation; a pyrene (including any of the corresponding derivative compounds disclosed in U.S. Pat. No. 5,132,432, incorporated by reference), an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine, a carbocyanine (including any corresponding compounds in U.S. Pat. Nos. 4,981,977; 5,268,486; 5,569,587; 5,569,766; 5,486,616; 5,627,027; 5,808,044; 5,877,310; 6,002,003; 6,004,536; 6,008,373; 6,043,025; 6,127,134; 6,130,094; 6,133,445; 6,664,047; 6,974,873 and 6,977,305; and publications WO 02/26891, WO 97/40104, WO 99/51702, WO 01/21624; EP 1 065 250 A1, incorporated by reference), a carbostyryl, a porphyrin, a salicylate, an anthranilate, an azulene, a perylene, a pyridine, a quinoline, a borapolyazaindacene (including any corresponding compounds disclosed in U.S. Pat. Nos. 4,774,339; 5,187,288; 5,248,782; 5,274,113; and 5,433,896, incorporated by reference), a xanthene (including any corresponding compounds disclosed in U.S. Pat. Nos. 6,162,931; 6,130,101; 6,229,055; 6,339,392; 5,451,343 and 6,716,979, incorporated by reference), an oxazine (including any corresponding compounds disclosed in U.S. Pat. No. 4,714,763, incorporated by reference) or a benzoxazine, a carbazine (including any corresponding compounds disclosed in U.S. Pat. No. 4,810,636, incorporated by reference), a phenalenone, a coumarin (including an corresponding compounds disclosed in U.S. Pat. Nos. 5,696,157; 5,459,276; 5,501,980 and 5,830,912, incorporated by reference), a benzofuran (including an corresponding compounds disclosed in U.S. Pat. Nos. 4,603,209 and 4,849,362, incorporated by reference) and benzphenalenone (including any corresponding compounds disclosed in U.S. Pat. No. 4,812,409, incorporated by reference) and derivatives thereof. As used herein, oxazines include resorufins (including any corresponding compounds disclosed in 5,242,805, incorporated by reference), aminooxazinones, diaminooxazines, and their benzo-substituted analogs. Additional labeling moieties include, but are not limited to, those compounds that are described in United States Patent Publication No. 2006/0280652, published 14 Dec. 2006, and PCT Publication No. WO 2006/025887, which are incorporated by reference.

When the fluorophore is a xanthene, the fluorophore is optionally a fluorescein, a rhodol (including any corresponding compounds disclosed in U.S. Pat. Nos. 5,227,487 and 5,442,045, incorporated by reference), or a rhodamine (including any corresponding compounds in U.S. Pat. Nos. 5,798,276; 5,846,737 and 6,562,632, incorporated by reference). As used herein, fluorescein includes benzo- or dibenzofluoresceins, seminaphthofluoresceins, or naphthofluoresceins. Similarly, as used herein rhodol includes seminaphthorhodafluors (including any corresponding compounds disclosed in U.S. Pat. No. 4,945,171, incorporated by reference). Alternatively, the fluorophore is a xanthene that is bound via a linkage that is a single covalent bond at the 9-position of the xanthene. Preferred xanthenes include derivatives of 3H-xanthen-6-ol-3-one attached at the 9-position, derivatives of 6-amino-3H-xanthen-3-one attached at the 9-position, or derivatives of 6-amino-3H-xanthen-3-imine attached at the 9-position.

Fluorophores for use in the present invention include, but are not limited to, xanthene (rhodol, rhodamine, fluorescein and derivatives thereof) coumarin, cyanine, pyrene, oxazine and borapolyazaindacene. Most preferred are sulfonated xanthenes, fluorinated xanthenes, sulfonated coumarins, fluorinated coumarins and sulfonated cyanines. The choice of the fluorophore will determine the absorption and fluorescence emission properties of the GGBP or other labeling reagent complex. Physical properties of a fluorophore label include spectral characteristics (absorption, emission and stokes shift), fluorescence intensity, lifetime, polarization and photo-bleaching rate all of which can be used to distinguish one fluorophore from another.

Typically the fluorophore contains one or more aromatic or heteroaromatic rings, that are optionally substituted one or more times by a variety of substituents, including without limitation, halogen, nitro, cyan, alkyl, perfluoroalkyl, alkoxy, alkenyl, alkynyl, cycloalkyl, arylalkyl, acyl, aryl or heteroaryl ring system, benzo, or other substituents typically present on fluorophores known in the art.

Specific examples of fluorophore labels are selected from the group consisting of fluorescein, coumarins, rhodamines, 5-TMRIA (tetramethylrhodamine-5-iodoacetamide), (9-(2 (or 4)-(N-(2-maleimdylethyl)-sulfonamidyl)-4(or 2)-sulfophenyl)-2,3,6,7,12,13,16,17-octahydro-(1H,5H,11H,15H-xantheno(2,3,4-ij:5,6,7-i'j')diquinolizin-18-ium salt) (Texas Red®), 2-(5-(1-(6-(N-(2-maleimdylethyl)-amino)-6-oxo-hexyl)-1,3-dihydro-3,3-dimethyl-5-sulfo-2H-indol-2-ylidene)-1,3-propyldienyl)-1-ethyl-3,3-dimethyl-5-sulfo-3H-indolium salt (Cy™ 3), N,N'-dimethyl-N-(iodoacetyl)-N'-(7-nitrobenz-2-oxa-1,3-diazol-4-yl)ethylenediamine (IANBD amide), N-((2-(iodoacetoxy)ethyl)-N-methyl amino-7-nitrobenz-2-oxa-1,3-diazole (IANBD ester), 6-acryloyl-2-dimethylaminonaphthalene (acrylodan), pyrene, 6-amino-2,3-dihydro-2-(2-((iodoacetyl)amino) ethyl)-1,3-dioxo-1H-benz(de)isoquinoline-5,8-disulfonic acid salt (lucifer yellow), 2-(5-(1-(6-(N-(2-maleimdylethyl)-amino)-6-oxohexyl)-1,3-dihydro-3,3-dimethyl-5-sulfo-2H-indol-2-ylidene)-1,3-pentadienyl)-1-ethyl-3,3-dimethyl-5-sulfo-3H-indolium salt (Cy™ 5), 4-(5-(4-dimethylaminophenyl)oxazol-2-yl)phenyl-N-(2-bromoacetamidoethyl)sulfonamide (Dapoxyl® (2-bromoacetamidoethyl)sulfonamide)), (N-(4,4-difluoro-1,3,5,7-tetramethyl-4-bora-3a,4a-diaza-s-indacene-2-yl)iodoacetamide (BODIPY® 507/545 IA), N-(4,4-difluoro-5,7-diphenyl-4-bora-3a,4a-diaza-s-indacene-3-propionyl)-N'-iodoacetylethylenediamine (BODIPY® 530/550 IA), 5-((((2-iodoacetyl)amino)ethyl)amino)naphthalene-1-sulfonic acid (1,5-IAEDANS), and carboxy-X-rhodamine, 5/6-iodoacetamide (XRIA 5,6). Another example of a label is BODIPY®-FL-hydrazide. Other luminescent labels include lanthanides such as europium (Eu3+) and terbium (Tb3+), as well as metal-ligand complexes of ruthenium [Ru(II)], rhenium [Re(I)], or osmium [Os(II)], typically in complexes with diimine ligands such as phenanthroline. United States Patent Publication No. 2006/028652, published 14 Dec. 2006, which is incorporated by reference, discloses additional fluorophores that may be useful for the present invention.

In addition to fluorophores, enzymes also find use as labels. Enzymes are desirable labels because amplification of the detectable signal can be obtained resulting in increased assay sensitivity. The enzyme itself may not produce a detectable signal but is capable of generating a signal by, for example, converting a substrate to produce a detectable signal, such as a fluorescent, colorimetric or luminescent signal. Enzymes amplify the detectable signal because one enzyme on a labeling reagent can result in multiple substrates being converted to a detectable signal. This is advantageous where there is a low quantity of target present in the sample or a fluorophore does not exist that will give comparable or stronger signal than the enzyme. The enzyme substrate is selected to yield the preferred measurable product, e.g., colorimetric, fluorescent or chemiluminescence. Such substrates are extensively used in the art, many of which are described in the MOLECULAR PROBES HANDBOOK, supra.

In a specific embodiment, a colorimetric or fluorogenic substrate and enzyme combination uses oxidoreductases such as horseradish peroxidase and a substrate such as 3,3'-diaminobenzidine (DAB) and 3-amino-9-ethylcarbazole (AEC), which yield a distinguishing color (brown and red, respectively). Other colorimetric oxidoreductase substrates that yield detectable products include, but are not limited to: 2,2-azino-bis(3-ethylbenzothiazoline-6-sulfonic acid) (ABTS), o-phenylenediamine (OPD), 3,3',5,5'-tetramethylbenzidine (TMB), o-dianisidine, 5-aminosalicylic acid, 4-chloro-1-naphthol. Fluorogenic substrates include, but are not limited to, homovanillic acid or 4-hydroxy-3-methoxyphenylacetic acid, reduced phenoxazines and reduced benzothiazines, including Amplex® Red reagent and its variants (U.S. Pat. No. 4,384,042) and reduced dihydroxanthenes, including dihydrofluoresceins (U.S. Pat. No. 6,162,931, incorporated by reference) and dihydrorhodamines including dihydrorhodamine 123. Peroxidase substrates that are tyramides (U.S. Pat. Nos. 5,196,306; 5,583,001 and 5,731,158, incorporated by reference) represent a unique class of peroxidase substrates in that they can be intrinsically detectable before action of the enzyme but are "fixed in place" by the action of a peroxidase in the process described as tyramide signal amplification (TSA). These substrates are extensively utilized to label targets in samples that are cells, tissues or arrays for their subsequent detection by microscopy, flow cytometry, optical scanning and fluorometry.

Another preferred colorimetric (and in some cases fluorogenic) substrate and enzyme combination uses a phosphatase enzyme such as an acid phosphatase, an alkaline phosphatase or a recombinant version of such a phosphatase in combination with a colorimetric substrate such as 5-bromo-6-chloro-3-indolyl phosphate (BCIP), 6-chloro-3-indolyl phosphate, 5-bromo-6-chloro-3-indolyl phosphate, p-nitrophenyl phosphate, or o-nitrophenyl phosphate or with a fluorogenic substrate such as 4-methylumbelliferyl phosphate, 6,8-difluoro-7-hydroxy-4-methylcoumarinyl phosphate (DiFMUP, U.S. Pat. No. 5,830,912, incorporated by reference) fluorescein diphosphate, 3-O-methylfluorescein phosphate, resorufin phosphate, 9H-(1,3-dichloro-9,9-dimethylacridin-2-one-7-yl) phosphate (DDAO phosphate), or ELF 97, ELF 39 or related phosphates (U.S. Pat. Nos. 5,316,906 and 5,443,986, incorporated by reference).

Additional enzymes include, but are not limited to, hydrolases such as cholinesterases and peptidases, oxidases such as cytochrome oxidases, and reductases for which suitable substrates are known. Specific embodiments of the present invention comprise enzymes and their appropriate substrates to produce a chemiluminescent signal, such as, but not limited to, natural and recombinant forms of luciferases and aequorins. Chemiluminescence-producing substrates for phosphatases, glycosidases and oxidases such as those containing stable dioxetanes, luminol, isoluminol and acridinium esters are additionally useful.

Additional embodiments comprise haptens such as biotin. Biotin is useful because it can function in an enzyme system to further amplify the detectable signal, and it can function as a tag to be used in affinity chromatography for isolation purposes. For detection purposes, an enzyme conjugate that has affinity for biotin is used, such as avidin-HRP. Subsequently a peroxidase substrate is added to produce a detectable signal.

Haptens also include hormones, naturally occurring and synthetic drugs, pollutants, allergens, affector molecules, growth factors, chemokines, cytokines, lymphokines, amino acids, peptides, chemical intermediates, nucleotides and the like.

Fluorescent proteins also find use as labels for the labeling reagents of the present invention. Thus, in one specific embodiment, the reference GGBP is a fusion protein comprising a functional GGBP and a fluorescent protein, where the fluorescent protein acts as at least one label. The modified thermostable functional GGBPs would, in turn, comprise a fluorescent protein. In another embodiment, the modified proteins of the current invention may comprise two, three, four or more fluorescent proteins. If the fusion proteins of the current invention contain more than one fluorescent protein, the fluorescent proteins may or may not be chemically identical. Fluorescent proteins are easily recognized in the art. Examples of fluorescent proteins that are part of fusion proteins of the current invention include, but are not limited to, green fluorescent proteins (GFP, AcGFP, ZsGreen), red-shifted GFP (rs-GFP), red fluorescent proteins (RFP, including DsRed2, HcRed1, dsRed-Express), yellow fluorescent proteins (YFP, Zsyellow), cyan fluorescent proteins (CFP, AmCyan), a blue fluorescent protein (BFP) and the phycobiliproteins, as well as the enhanced versions and mutations of these proteins. For some fluorescent proteins enhancement indicates optimization of emission by increasing the proteins' brightness or by creating proteins that have faster chromophore maturation. These enhancements can be achieved through engineering mutations into the fluorescent proteins.

The fluorescent proteins, especially phycobiliprotein, are particularly useful for creating tandem dye labeled labeling reagents. In one embodiment of the current invention, therefore, the measurable signal of the fusion protein is actually a transfer of excitation energy (resonance energy transfer) from a donor molecule to an acceptor molecule. In particular, the resonance energy transfer is in the form of fluorescence resonance energy transfer (FRET). When the modified proteins of the present invention utilize FRET to measure of quantify analyte(s), the fusion protein can be the donor or the acceptor. The terms "donor" and "acceptor," when used in relation to FRET, are readily understood in the art. Namely, a donor is the molecule that will absorb a photon of light and subsequently initiate energy transfer to the acceptor molecule. The acceptor molecule is the molecule that receives the energy transfer initiated by the donor and, in turn, emits a photon of light. The efficiency of FRET is dependent upon the distance between the two fluorescent partners and can be expressed mathematically by: $E=R_0^6/(R_0^6+r^6)$, where E is the efficiency of energy transfer, r is the distance (in Angstroms) between the fluorescent donor/acceptor pair and $R_0$ is the Förster distance (in Angstroms). The Förster distance, which can be determined experimentally by readily available techniques in the art, is the distance at which FRET is half of the maximum possible FRET value for a given donor/acceptor pair. A particularly useful combination is the phycobiliproteins disclosed in U.S. Pat. Nos. 4,520,110; 4,859,582; 5,055,556, incorporated by reference, and the sulforhodamine fluorophores disclosed in 5,798,276, or the sulfonated cyanine fluorophores disclosed in U.S. Pat. Nos. 6,977,305 and 6,974,873; or the sulfonated xanthene derivatives disclosed in U.S. Pat. No. 6,130,101, incorporated by reference and those combinations disclosed in U.S. Pat. No. 4,542,104, incorporated by reference.

Other types of fusion proteins provided by the present invention include but are not limited to, fusions with secretion signals and other heterologous functional regions. Thus, for instance, a region of additional amino acids, particularly charged amino acids, may be added to the N-terminus of the protein to improve stability and persistence in the host cell, during purification or during subsequent handling and storage. Also, a region also may be added to the protein to facilitate purification. For example, the reference protein and/or thermostable protein may comprise "histidine tags" ("his tags") or "lysine tags". Example of histidine tags include, but are not limited to hexaH, heptaH and hexaHN. Additional examples of purification tags are disclosed in Waugh, D. S., *Trends in Biotechnology*, 23(6):316-320 (June 2005), and Gaberc-Porekar V. and Menart, V., *J. Biochem. Biophys. Methods.* 49:335-360 (2001), which are incorporated by reference. Examples of lysine tags include but are not limited to pentaL, heptaL and FLAG. Additional examples of solubility tags are also disclosed in Waugh, D. S., *Trends in Biotechnology*, 23(6) 316-320 (June 2005). Such regions may be removed prior to final preparation of the protein. The addition of peptide moieties to proteins, whether to engender secretion or excretion, to improve stability and to facilitate purification, among others, is a familiar and routine technique in the art and may include modifying amino acids at the terminus to accommodate the tags. For example in SEQ ID NOs: 3 and 4, the C-terminus amino acid (lysine) may be modified to, for example, arginine and serine to accommodate a tag. Of course, the amino acid residues of the N-terminus may also be modified to accommodate tags. One particularly useful fusion protein comprises a heterologous region from immunoglobulin that can be used solubilize proteins. For example, EP A0464 533 discloses fusion proteins comprising various portions of constant region of immunoglobin molecules together with another human protein or part thereof. In many cases, the Fc part in a fusion protein is thoroughly advantageous for use in therapy and diagnosis and thereby results, for example, in improved pharmacokinetic properties (EP A0232 262). On the other hand, for some uses, it would be desirable to be able to delete the Fc part after the fusion protein has been expressed, detected and purified in the advantageous manner described.

The fusion proteins of the current invention can be recovered and purified from recombinant cell cultures by well-known methods including, but not limited to, ammonium sulfate or ethanol precipitation, acid extraction, anion or cation exchange chromatography, phosphocellulose chromatography, hydrophobic interaction chromatography, affinity chromatography, e.g., immobilized metal affinity chromatography (IMAC), hydroxylapatite chromatography and lectin chromatography. High performance liquid chromatography ("HPLC") may also be employed for purification. Well-known techniques for refolding protein may be employed to regenerate active conformation when the fusion protein is denatured during isolation and/or purification.

Fusion proteins of the present invention include, but are not limited to, products of chemical synthetic procedures and products produced by recombinant techniques from a prokaryotic or eukaryotic host, including, for example, bacterial, yeast, higher plant, insect and mammalian cells. Depending upon the host employed in a recombinant production procedure, the fusion proteins of the present invention may be glycosylated or may be non-glycosylated. In addition, fusion proteins of the invention may also include an initial modified methionine residue, in some cases as a result of host-mediated processes.

Modified thermostable GGBPs may also be modified, either by natural processes, such as post-translational processing, or by chemical modification techniques, which are well known in the art. Such modifications are well described in basic texts and in more detailed monographs, as well as in voluminous research literature. Modifications can occur anywhere in the polypeptide chain, including the peptide backbone, the amino acid side-chains and the amino or carboxyl termini. It will be appreciated that the same type of modification may be present in the same or varying degrees at several sites in a given polypeptide or protein. Also, a given polypeptide or protein may contain more than one modification. Examples of modifications include, but are not limited to, glycosylation, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Polypeptides or proteins may even be branched as a result of ubiquitination, and they may be cyclic, with or without branching. (See, e.g., T. E. Creighton, *Proteins—Structure And Molecular Properties,* 2nd Ed., W. H. Freeman and Company, New York (1993); Wold, F., "Posttranslational Protein Modifications: Perspectives and Prospects", in *Posttranslational Covalent Modification Of Proteins*, B. C. Johnson, Ed., Academic Press, New York (1983); Seifter et al., *Methods in Enzymol,* 182:626-646 (1990) and Rattan et al., *Ann NY Acad. Sci.,* 663:48-62 (1992), all of which are incorporated herein by reference.

The reference proteins of the present invention may be modified by techniques well known to those of skill in the art. Examples of such techniques include, but are not limited to, mutagenesis and direct synthesis of the modified proteins.

The modified thermostable proteins of the present invention may be isolated. As used herein, an "isolated protein" is intended to mean a protein that has been completely or partially removed from its native environment. For example, polypeptides that have been removed or purified from cells are considered isolated. In addition, recombinantly produced polypeptides molecules contained in host cells are considered isolated for the purposes of the present invention. Similarly, proteins that have been synthesized are considered to be isolated proteins.

The invention also relates to isolated nucleic acids and to constructs comprising these nucleic acids. The nucleic acids of the invention can be DNA or RNA, for example, mRNA. The nucleic acid molecules can be double-stranded or single-stranded; single stranded RNA or DNA can be the coding, or sense, strand or the non-coding, or antisense, strand. In particular, the nucleic acids may encode the polypeptide of the invention. If desired, the nucleotide sequence of the isolated nucleic acid can include additional non-coding sequences such as non-coding 3' and 5' sequences (including regulatory sequences, for example). Additionally, the nucleic acids of the invention can be used as a nucleic acid comprising a marker sequence, for example, a nucleotide sequence which encodes a polypeptide to assist in isolation or purification of the polypeptide. Representative sequences include, but are not limited to, those which encode a glutathione-S-transferase (GST) fusion protein, a poly-histidine (e.g., $His_6$), poly-HN, poly-lysine, hemagglutinin, HSV-Tag, for example.

The nucleic acid molecules of the invention are "isolated." As used herein, an "isolated" nucleic acid molecule or nucleotide sequence is intended to mean a nucleic acid molecule or nucleotide sequence which is not flanked by nucleotide sequences which normally flank the gene or nucleotide sequence (as in genomic sequences) and/or has been completely or partially removed from its native environment (e.g., a cell, tissue). For example, an isolated nucleic acid of the invention may be substantially isolated with respect to the complex cellular milieu in which it naturally occurs. In some instances, the isolated material will form part of a composition (for example, a crude extract containing other substances), buffer system or reagent mix. In other circumstances, the material may be purified to essential homogeneity, for example as determined by PAGE or column chromatography such as HPLC. Thus, an isolated nucleic acid molecule or nucleotide sequence can include a nucleic acid molecule or nucleotide sequence which is synthesized chemically, using recombinant DNA technology or using any other suitable method. Therefore, a recombinant nucleic acid contained in a vector is included in the definition of "isolated" as used herein. Also, isolated nucleotide sequences include recombinant nucleic acid molecules (e.g., DNA, RNA) in heterologous organisms, as well as partially or substantially purified nucleic acids in solution. Both in vivo and in vitro RNA transcripts of a DNA molecule of the present invention are also encompassed by "isolated" nucleotide sequences.

The invention also encompasses variations of the nucleotide sequences of the invention, such as those encoding functional fragments or functional derivatives of the polypeptides as described below. Such variations can be naturally-occurring, or non-naturally-occurring, such as those induced by various mutagens and mutagenic processes. Intended variations include, but are not limited to, addition, deletion and substitution of one or more nucleotides which can result in conservative or non-conservative amino acid changes, including additions and deletions. In one aspect of the present invention, the variations of the nucleic acid molecules and proteins of the present invention comprise modifications within the binding domain are silent or conserved; that is, the modification do not substantially alter the characteristics or activity of the encoded polypeptide relative to the modified thermostable GGBPs of the present invention. In another embodiment, the variations of the nucleic acid molecules and proteins of the present invention comprise modifications within the binding domain that are not silent or conserved; that is, the modification may substantially alter the characteristics or activity of the encoded polypeptide relative to the modified thermostable GGBPs of the present invention.

The invention described herein also relates to fragments of the isolated nucleic acid molecules described herein. The term "fragment" is intended to encompass a portion of a nucleotide sequence described herein which is from at least about 25 contiguous nucleotides to at least about 50 contiguous nucleotides or longer in length. Such fragments may be useful as probes and primers. In particular, primers and probes may selectively hybridize to the nucleic acid molecule encoding the polypeptides described herein. For example, fragments which encode polypeptides that retain activity, as described below, are particularly useful.

The invention also pertains to nucleic acid molecules which hybridize under high stringency hybridization conditions, such as for selective hybridization, to the nucleotide sequences described herein (e.g., nucleic acid molecules which specifically hybridize to a nucleotide sequence encoding polypeptides described herein and encode a thermostable GGBP). Hybridization probes include synthetic oligonucleotides which bind in a base-specific manner to a complementary strand of nucleic acid. Suitable probes include polypeptide nucleic acids, as described in Nielsen et al., Science, 254:1497-1500 (1991).

Such nucleic acid molecules can be detected and/or isolated by specific hybridization e.g., under high stringency conditions. "Stringency conditions" for hybridization is a term of art which refers to the incubation and wash conditions, e.g., conditions of temperature and buffer concentration, which permit hybridization of a particular nucleic acid to a second nucleic acid; the first nucleic acid may be perfectly complementary, i.e., 100%, to the second, or the first and second may share some degree of complementarity which is less than perfect, e.g., 60%, 75%, 85%, 95% or more. For example, certain high stringency conditions can be used which distinguish perfectly complementary nucleic acids from those of less complementarity.

"High stringency conditions", "moderate stringency conditions" and "low stringency conditions" for nucleic acid hybridizations are explained in *Current Protocols in Molecular Biology*, John Wiley & Sons, (1998)), which is incorporated by reference. The exact conditions which determine the stringency of hybridization depend not only on ionic strength, e.g., 0.2×SSC, 0.1×SSC of the wash buffers, temperature, e.g., room temperature, 42° C., 68° C., etc., and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. Thus, high, moderate or low stringency conditions may be determined empirically.

By varying hybridization conditions from a level of stringency at which no hybridization occurs to a level at which hybridization is first observed, conditions which will allow a given sequence to hybridize with the most similar sequences in the sample can be determined.

Exemplary conditions are described in Krause, M. H. and S. A. Aaronson, *Methods in Enzymology,* 200:546-556 (1991), which is incorporated by reference. Washing is the step in which conditions are usually set so as to determine a minimum level of complementarity of the hybrids. Generally, starting from the lowest temperature at which only homologous hybridization occurs, each degree (° C.) by which the final wash temperature is reduced, while holding SSC concentration constant, allows an increase by 1% in the maximum extent of mismatching among the sequences that hybridize. Generally, doubling the concentration of SSC results in an increase in Tm. Using these guidelines, the washing temperature can be determined empirically for high, moderate or low stringency, depending on the level of mismatch sought. Exemplary high stringency conditions include, but are not limited to, hybridization in 50% formamide, 1 M NaCl, 1% SDS at 37° C., and a wash in 0.1×SSC at 60° C. Example of progressively higher stringency conditions include, after hybridization, washing with 0.2×SSC and 0.1% SDS at about room temperature (low stringency conditions); washing with 0.2×SSC, and 0.1% SDS at about 42° C. (moderate stringency conditions); and washing with 0.1×SSC at about 68° C. (high stringency conditions). Washing can be carried out using only one of these conditions, e.g., high stringency conditions, washing may encompass two or more of the stringency conditions in order of increasing stringency. Optimal conditions will vary, depending on the particular hybridization reaction involved, and can be determined empirically.

Equivalent conditions can be determined by varying one or more of the parameters given as an example, as known in the art, while maintaining a similar degree of identity or similarity between the target nucleic acid molecule and the primer or probe used. Hybridizable nucleotide sequences are useful as probes and primers for identification of organisms comprising a nucleic acid of the invention and/or to isolate a nucleic acid of the invention, for example. The term "primer" is used herein as it is in the art and refers to a single-stranded oligonucleotide which acts as a point of initiation of template-directed DNA synthesis under appropriate conditions in an appropriate buffer and at a suitable temperature. The appropriate length of a primer depends on the intended use of the primer, but typically ranges from about 15 to about 30 nucleotides. Short primer molecules generally require cooler temperatures to form sufficiently stable hybrid complexes with the template. A primer need not reflect the exact sequence of the template, but must be sufficiently complementary to hybridize with a template. The term "primer site" refers to the area of the target DNA to which a primer hybridizes. The term "primer pair" refers to a set of primers including a 5' (upstream) primer that hybridizes with the 5' end of the DNA sequence to be amplified and a 3' (downstream) primer that hybridizes with the complement of the 3' end of the sequence to be amplified.

The nucleic acids described herein can be amplified by methods known in the art. For example, amplification can be accomplished by the polymerase chain reaction (PCR). See PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Mattila et al., Nucleic Acids Res. 19:4967 (1991); Eckert et al., PCR Methods and Applications 1:17 (1991); PCR (eds. McPherson et al., IRL Press, Oxford); and U.S. Pat. No. 4,683,202, all of which are incorporated by reference. Other suitable amplification methods include the ligase chain reaction (LCR) (see Wu and Wallace, *Genomics,* 4:560 (1989), Landegren et al., *Science,* 241:1077 (1988), both of which are incorporated by reference), transcription amplification (Kwoh et al., *Proc. Natl. Acad. Sci. USA,* 86:1173 (1989), incorporated by reference), and self-sustained sequence replication (Guatelli et al., *Proc. Nat. Acad. Sci. USA,* 87:1874 (1990) incorporated by reference) and nucleic acid based sequence amplification (NASBA).

The present invention also relates to vectors that include DNA molecules of the present invention, host cells that are genetically engineered with vectors of the invention and the production of proteins of the invention by recombinant techniques.

In accordance with this aspect of the invention, the vector may be, for example, a plasmid vector, a single- or double-stranded phage vector, or a single- or double-stranded RNA or DNA viral vector. Such vectors may be introduced into cells as polynucleotides, preferably DNA, by well-known techniques for introducing DNA and RNA into cells. Viral vectors may be replication competent or replication defective. In the latter, case viral propagation generally will occur only in complementing host cells.

Preferred among vectors, in certain respects, are those for expression of polynucleotides and proteins of the present invention. Generally, such vectors comprise cis-acting control regions effective for expression in a host operatively linked to the polynucleotide to be expressed. Appropriate trans-acting factors are supplied by the host, supplied by a complementing vector or supplied by the vector itself upon introduction into the host.

A great variety of expression vectors can be used to express the proteins of the invention. Such vectors include chromosomal, episomal and virus-derived vectors, e.g., vectors derived from bacterial plasmids, from bacteriophage, from yeast episomes, from yeast chromosomal elements, from viruses such as adeno-associated virus, lentivirus, baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. All may be used for expression in accordance with this aspect of the present invention. Generally, any vector suitable to maintain, propagate or express polynucleotides or proteins in a host may be used for expression in this regard.

The DNA sequence in the expression vector is operatively linked to appropriate expression control sequence(s) including, for instance, a promoter to direct mRNA transcription. Representatives of such promoters include, but are not limited to, the phage lambda PL promoter, the *E. coli* lac, trp and tac promoters, HIV promoters, the SV40 early and late promoters and promoters of retroviral LTRs, to name just a few of the well-known promoters. In general, expression constructs will contain sites for transcription, initiation and termination and, in the transcribed region, a ribosome binding site for translation. The coding portion of the mature transcripts expressed by the constructs will include a translation initiating AUG at the beginning and a termination codon (UAA, UGA or UAG) appropriately positioned at the end of the polypeptide to be translated.

In addition, the constructs may contain control regions that regulate, as well as engender expression. Generally, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, and tetracycline, kanamycin or ampicillin resistance genes for culturing E. coli and other bacteria.

The vector containing the appropriate DNA sequence, as well as an appropriate promoter, and other appropriate control sequences, may be introduced into an appropriate host using a variety of well-known techniques suitable to expression therein of a desired polypeptide. Representative examples of appropriate hosts include bacterial cells, such as E. coli, Streptomyces and Salmonella typhimurium cells; fungal cells, such as yeast cells; insect cells such as Drosophila S2 and Spodoptera Sf9 cells; animal cells such as CHO, COS and Bowes melanoma cells; and plant cells. Hosts for of a great variety of expression constructs are well known, and those of skill in the art will be enabled by the present disclosure to select an appropriate host for expressing one of the proteins of the present invention.

Examples of vectors for use in bacteria include, but are not limited to, pQE70, pQE60 and pQE-9, available from Qiagen (Valencia, Calif.); pVEXK-HN-K6 available from Nature Technology Corp (Lincoln, Nebr.), pBS vectors, Phagescript vectors, Bluescript vectors, pNHSA, pNH16a, pNH18A, pNH46A, available from Stratagene (La Jolla, Calif.); ptrc99a, pKK223-3, pKK233-3, pDR540, pRIT5 available from Amersham-Pharmacia Biotech (Piscataway, N.J.); and pEGFP-C1, pEYFP-C1, pDsRed2-C1, pDsRed2-Express-C1, and pAcGFP1, pAcGFP-C1, pZsYellow-C1, available from Clontech (Palo Alto, Calif.). Examples of eukaryotic vectors include, but are not limited to, pW-LNEO, pSV2CAT, pOG44, pXT1 and pSG available from Stratagene; pSVK3, pBPV, pMSG and pSVL available from Pharmacia; and pCMVDsRed2-express, pIRES2-DsRed2, pDsRed2-Mito, pCMV-EGFP available from Clontech. Many other commercially available and well-known vectors are available to those of skill in the art. Selection of appropriate vectors and promoters for expression in a host cell is a well-known procedure and the requisite techniques for expression vector construction, introduction of the vector into the host and expression in the host are routine skills in the art.

The present invention also relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. The host cell can be stably or transiently transfected with the construct. The polynucleotides may be introduced alone or with other polynucleotides. Such other polynucleotides may be introduced independently, co-introduced or introduced joined to the polynucleotides of the invention.

Introduction of a construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods in Molecular Biology (1986), incorporated by reference.

The current invention also relates to methods of producing a modified thermostable GGBP comprising culturing the host cells of the invention under conditions such that the modified thermostable GGBP is expressed, and recovering said protein. The culture conditions required to express the proteins of the current invention are dependent upon the host cells that are harboring the polynucleotides of the current invention. The culture conditions for each cell type are well-known in the art and can be easily optimized, if necessary. For example, a nucleic acid encoding a polypeptide of the invention, or a construct comprising such nucleic acid, can be introduced into a suitable host cell by a method appropriate to the host cell selected, e.g., transformation, transfection, electroporation, infection, such that the nucleic acid is operably linked to one or more expression control elements as described herein. Host cells can be maintained under conditions suitable for expression in vitro or in vivo, whereby the encoded polypeptide is produced. For example host cells may be maintained in the presence of an inducer, suitable media supplemented with appropriate salts, growth factors, antibiotic, nutritional supplements, etc., which may facilitate protein expression. In additional embodiments, the modified thermostable GGBPs of the invention can be produced by in vitro translation of a nucleic acid that encodes the modified thermostable GGBP, by chemical synthesis or by any other suitable method. If desired, the modified thermostable GGBP can be isolated from the host cell or other environment in which the protein is produced or secreted. It should therefore be appreciated that the method of producing the modified thermostable GGBPs encompasses expression of the polypeptide in a host cell of a transgenic animal or plant. See U.S. Pat. Nos. 6,013,857, 5,990385, and 5,994,616, which are incorporated by reference.

The modified thermostable GGBPs of the present invention are useful in a variety of applications, such as industrial processes, and as components of biosensors to detect, monitor or measure analyte quantities in a sample. Biosensors are devices capable of providing specific quantitative or semi-quantitative analytical information using a biological recognition element, such as a GGBP or a modified GGBP, which is combined with a transducing (detecting) element. Examples of analytes include, but are not limited to, carbohydrates such as monosaccharides, disaccharides, oligosaccharides and polysaccharides, proteins, peptides and amino acids, including, but not limited to, oligopeptides, polypeptides and mature proteins, nucleic acids, oligonucleotides, polynucleotides, lipids, fatty acids, lipoproteins, proteoglycans, glycoproteins, organic compounds, inorganic compounds, ions, and synthetic and natural polymers. In one embodiment, the analyte is a carbohydrate. In particular, the carbohydrate analyte may be a sugar, such as glucose, galactose or ribose. More particularly, the analyte may be glucose.

The analyte is measured in a sample. As used herein, a sample can be any environment that may be suspected of containing the analyte to be measured. Thus, a sample includes, but is not limited to, a solution, a cell, a body fluid, a tissue or portion thereof, and an organ or portion thereof. When a sample includes a cell, the cell can be a prokaryotic or eukaryotic cell, for example, an animal cell. Examples of animal cells include, but are not limited to, insect, avian, and mammalian such as, for example, bovine, equine, porcine, canine, feline, human and nonhuman primates. The scope of the invention should not be limited by the cell type assayed. Examples of biological fluids to be assayed include, but are not limited to, blood, urine, saliva, synovial fluid, interstitial fluid, cerebrospinal fluid, lymphatic fluids, bile and amniotic fluid. The scope of the methods of the present invention should not be limited by the type of body fluid assayed. The terms "subject" and "patient" are used interchangeably herein and are used to mean an animal, particularly a mammal, more particularly a human or nonhuman primate.

The samples may or may not have been removed from their native environment. Thus, the portion of sample assayed need not be separated or removed from the rest of the sample or from a subject that may contain the sample. For example, the blood of a subject may be assayed for glucose without removing any of the blood from the patient. Of course, the sample may also be removed from its native environment. Furthermore, the sample may be processed prior to being assayed. For example, the sample may be diluted or concentrated; the sample may be purified and/or at least one compound, such as an internal standard, may be added to the sample. The sample may also be physically altered (e.g., centrifugation, affinity separation) or chemically altered (e.g., adding an acid, base or buffer, heating) prior to or in conjunction with the methods of the current invention. Processing also includes freezing and/or preserving the sample prior to assaying.

Another embodiment of the present invention relates to methods of sterilizing GGBPs. Methods of sterilizing periplasmic binding proteins (PBPs) are described in WO 2007/022485 published Feb. 22, 2007, which is hereby incorporated by reference. Specifically, the sterilization methods of the present invention comprise exposing the thermostable GGBPs of the present invention to at least one radiation source.

In one embodiment of the present invention, the thermostable GGBPs are placed in the presence of at least one free radical scavenger prior to exposure to the radiation. Free radical scavengers are well known in the art, and the invention is not limited to identity of the scavenger to which the thermostable GGBP is exposed. Examples of free radical scavengers include but are not limited to ascorbic acid, glutathione, tocopherols and tocotrienols. Additional examples of free radical scavengers include enzymes such, but not limited to, super oxide dismutase, catalses and peroxidases. In one specific embodiment, the free radical scavenger is sodium ascorbate. In more specific embodiments, the sodium ascorbate is present in concentrations of at least about 5 mM, 10 mM, 15 mM, 25 mM, 35 mM, 50 mM, 75 mM, 100 mM, 125 mM, 150 mM, mM, 200 mM, 250 mM, 300 mM or more. For example, solutions of an acrylodan-labeled thermostable GGBP of the invention (100 µM) can be prepared in phosphate buffered saline containing 0, 25, or 200 mM L (+)-ascorbic acid sodium salt. Sterilization can then be performed with gamma or e-beam irradiation (e.g. ~10 to ~20 kGy).

The thermostable GGBPs may also be placed into devices, such as, but not limited to biosensors. In one embodiment, the biosensors comprise a matrix that entraps the thermostable GGBPs. As used herein, "matrix" refers to essentially a three-dimensional environment which has at least one binding molecule immobilized therein for the purpose of measuring a detectable signal from ligand-protein interaction. Examples of matrices that are capable of entrapping the theromstable GGBPs are disclosed in United States Patent Publication No. 2005/0923155, published 27 Oct. 2005, which is incorporated by reference. The relationship between the constituents of the matrix and the thermostable GGBPs include, but are not limited to covalent, ionic, and van der Wals interactions and combinations thereof. The spatial relationship between the matrix and thermostable GGBPs includes heterogeneous and homogeneous distribution within and or upon any or all of the matrix volume. The matrix may be comprised of organic, inorganic, glass, metal, plastic, or combinations thereof. The matrix may also allow the biosensor to be incorporated at the distal end of a fiber or other small minimally invasive probe to be inserted within the tissue of a patient, to enable an episodic, continuous, or programmed reading to the patient. Information from the biosensor to the patient may be provided, for example, by telemetry, visual, audio, or other means known in the art, for example, as taught in U.S. Pat. No. 5,517,313, U.S. Pat. No. 5,910,661, U.S. Pat. No. 5,894,351, and U.S. Pat. No. 5,342,789 as well as United States Publication No. 2005/0113658 and in Beach, R. D., et al. IEEE Transactions on Instrumentation and Measurement (1999) 48, 6, p. 1239-1245, all of which are incorporated by reference. Information includes electrical, mechanical, and actinic radiation suitable for deriving analyte concentration or change in concentration, as is suitable.

As mentioned above, the thermostable GGBPs may be entrapped within a matrix, such as a hydrogel, which may then be used as an implantable device. As used herein, the term "entrap" and variations thereof is used interchangeably with "encapsulate" and is used to mean that the binding molecule is immobilized within or on the constituents of the matrix. The matrix can be in any desirable form or shape including one or more of disk, cylinder, patch, nanoparticle, microsphere, porous polymer, open cell foam, and combinations thereof, providing it permits permeability to analyte. The matrix additionally prevents leaching of the biosensor. The matrix permits light from optical sources or any other interrogating light to or from the reporter group to pass through the biosensor. When used in an in vivo application, the biosensor will be exposed to a substantially physiological range of analyte and determination or detection of a change in analyte concentration would be desired whereas the determination or detection includes continuous, programmed, and episodic detection means. Thus, in one embodiment of the present invention, the envisaged in vivo biosensor comprises at least one mutated binding protein in an analyte permeable entrapping or encapsulating matrix such that the mutated binding protein provides a detectable and reversible signal when the mutated binding protein is exposed to varying analyte concentrations, and the detectable and reversible signal can be related to the concentration of the analyte. The implantable biosensors may, in some embodiments, be implanted into or below the skin of a mammal's epidermal-dermal junction to interact with the interstitial fluid, tissue, or other biological fluids. In one specific embodiment, biosensor is implanted in the skin at a depth of less than about 2 mm. In a more specific embodiment, biosensor is implanted in the skin at a depth of less than about 1 mm. In an even more specific embodiment, biosensor is implanted in the skin at a depth of less than about 0.8 mm. Information from the implant to the patient may be provided, for example, by telemetry, visual, audio, or other means known in the art, as previously stated.

The matrix may be prepared from biocompatible materials or incorporates materials capable of minimizing adverse reactions with the body. Adverse reactions for implants include inflammation, protein fouling, tissue necrosis, immune response and leaching of toxic materials. Such materials or treatments are well known and practiced in the art, for example as taught by Quinn, C. P.; Pathak, C. P.; Heller, A.; Hubbell, J. A. Biomaterials 1995, 16(5), 389-396, and Quinn, C. A. P.; Connor, R. E.; Heller, A. Biomaterials 1997, 18(24), 1665-1670.

In one aspect of the present invention, the thermostable GGBPs may be entrapped or encapsulated within a matrix that is derived substantially from a hydrogel. The term "hydrogel" is used to indicate a water-insoluble, water-containing material.

Numerous hydrogels may be used in the present invention. The hydrogels may be, for example, polysaccharides such as agarose, dextran, carrageenan, alginic acid, starch, cellulose, or derivatives of these such as, e.g., carboxymethyl derivatives, or a water-swellable organic polymer such as, e.g., polyvinyl alcohol, polyacrylic acid, polyacrylamide, polyethylene glycol, copolymers of styrene and maleic anhydride, copolymers of vinyl ether and maleic anhydride and derivates thereof. Derivatives providing for covalently crosslinked networks are preferred. Synthesis and biomedical and pharmaceutical applications of hydrogels based on, comprising polypeptides, have been described by a number of researchers. (See, e.g. "Biosensors Fundamentals and Applications", edited by A. D. F. Turner, I. Karube and G. S. Wilson; published from Oxford University Press, in 1988). An exemplary hydrogel matrix derived from a water-soluble, UV crosslinkable polymer comprises poly(vinyl alcohol), N-methyl-4(4'-formylstyryl)pyridinium methosulphate acetal (CAS Reg. No. [107845-59-0]) available from PolyScience Warrington, Pa.

The polymers that are to be used in the matrices, such as hydrogels, used in the present invention may be functionalized. Of course, polymers used in other matrices may also be functionalized. That is, the polymers or monomers comprising the polymers should possess reactive groups such that the polymeric matrices, such as hydrogels, are amenable to chemical reactions, e.g., covalent attachment. As used herein and throughout, a "reactive group" is a chemical group that can chemically react with a second group. The reactive group of the polymer or monomers comprising the polymer may itself be an entire chemical entity or it may be a portion of an entire chemical entity, including, but not limited to single atoms or ions. Further, the second group with which the reactive group is capable of reacting can be the same or different from the reactive group of the polymer or monomers comprising the polymers. Examples of reactive groups include, but are not limited to, halogens, amines, amides, aldehydes, acrylates, vinyls, hydroxyls and carboxyls. In one embodiment, the polymers or monomers comprising the polymers of the hydrogel should be functionalized with carboxylic acid, sulfate, hydroxy or amine groups. In another embodiment of the present invention, the polymers or monomers comprising the polymers of the hydrogel are functionalized with one or more acrylate groups. In one particular embodiment, the acrylate functional groups are terminal groups. The reactive groups of the polymers or monomers comprising the polymers of the matrix may be reactive with any component of the matrix portion of the biosensor, such as, but not limited to, another polymer or monomer within the matrix, a binding protein and an additive.

Once formed, the core of any hydrogels used in the present invention should comprise polymers to form a polymeric hydrogel. Regardless of its application, the term "polymer" herein is used to refer to molecules composed of multiple monomer units. Suitable polymers which may be used in the present invention include, but are not limited to, one or more of the polymers selected from the group consisting of poly (vinyl alcohol), polyacrylamide, poly(N-vinyl pyrolidone), poly(ethylene oxide) (PEO), hydrolysed polyacrylonitrile, polyacrylic acid, polymethacrylic acid, poly(hydroxyethyl methacrylate), polyurethane polyethylene amine, poly(ethylene glycol) (PEG), cellulose, cellulose acetate, carboxy methyl cellulose, alginic acid, pectinic acid, hyaluronic acid, heparin, heparin sulfate, chitosan, carboxymethyl chitosan, chitin, collagen, pullulan, gellan, xanthan, carboxymethyl dextran, chondroitin sulfate, cationic guar, cationic starch as well as salts and esters thereof. The polymers of the matrix, such as a hydrogel, may also comprise polymers of two or more distinct monomers. Monomers used to create copolymers for use in the matrices include, but are not limited to acrylate, methacrylate, methacrylic acid, alkylacrylates, phenylacrylates, hydroxyalkylacrylates, hydroxyalkylmethacrylates, aminoalkylacrylates, aminoalkylmethacrylates, alkyl quaternary salts of aminoalkylacrylamides, alkyl quaternary salts of aminoalkylmethacrylamides, and combinations thereof. Polymer components of the matrix may, of course, include blends of other polymers. In one particular embodiment of the present invention, a hydrogel biosensor comprises a binding molecule and a matrix, with the matrix comprising a hydrogel of copolymers of (hydroxyethyl methacrylate) and methacrylic acid. In another particular embodiment of the present invention, a hydrogel biosensor comprises a binding molecule and a matrix hydrogel of copolymers of (hydroxyethyl methacrylate), methacrylic acid, and alkyl quaternary salts of methacrylamides.

The polymers used in the matrices can be modified to contain nucleophilic or electrophilic groups. Indeed, the polymers used in the present invention may further comprise polyfunctional small molecules that do not contain repeating monomer units but are polyfunctional, i.e., containing two or more nucleophilic or electrophilic functional groups. These polyfunctional groups may readily be incorporated into conventional polymers by multiple covalent bond-forming reactions. For example, PEG can be modified to contain one or more amino groups to provide a nucleophilic group. Examples of other polymers that contain one or more nucleophilic groups include, but are not limited to, polyamines such as ethylenediamine, tetramethylenediamine, pentamethylenediamine, hexamethylenediamine, bis-(2-hydroxyethyl) amine, bis-(2-aminoethyl)amine, and tris-(2-aminoethyl) amine. Examples of electrophilic groups include but are not limited to, succinimide esters, epoxides, hydroxybenzotriazole esters, oxycarbonylimidazoles, nitrophenyl carbonates, tresylates, mesylates, tosylates, carboxylates, and isocyanates. In one embodiment, the composition comprises a bis-amine-terminated poly(ethylene glycol).

The polymers should be capable of crosslinking, either physically or chemically, to form a matrix, such as a hydrogel. Physical crosslinking includes, but is not limited to, such non-chemical processes as radiation treatment such as electron beams, gamma rays, x-rays, ultraviolet light, anionic and cationic treatments. The crosslinking of the polymers may also comprise chemical crosslinking, such as covalent crosslinking. For example, a chemical crosslinking system may include, but is not limited to, the use of enzymes, which is well-known in the art. Another example of the chemical covalent crosslinking comprises the use of peroxide. Chemical crosslinking may occur when a crosslinking reagent reacts with at least two portions of a polymer to create a three-dimensional network. Covalent crosslinking may also occur when multifunctional monomers are used during the crosslinking process. For example, an acrylate monomer may be polymerized with a bifunctional acrylate monomer to form a crosslinked polymer. Any crosslinking reagent will be suitable for the present invention, provided the crosslinking reagent will at least partially dissolve in water or an organic solvent and can form the crosslinked polymer. For example, if the polymer is an amine-terminated PEG, the crosslinking reagent should be capable of reacting with the PEG-amine groups and be substantially soluble in water. In another example, (hydroxyethyl methacrylate) and methacrylic acid monomers can be polymerized with poly(ethylene glycol)-bis-alklyacrylate crosslinking agent in water or in dimethylformide to form polymeric hydrogels.

If the polymers to be crosslinked are functionalized with nucleophilic groups, such as amines (primary, secondary and tertiary), thiols, thioethers, esters, nitriles, and the like, the crosslinking reagent can be a molecule containing an electrophilic group. Examples of electrophilic groups have been described herein. Likewise, if polymers to be crosslinked are functionalized with electrophilic groups, the crosslinking reagent can be a molecule containing a nucleophilic group. It is understood that one skilled in the art can exchange the nucleophilic and electrophilic functional groups as described above without deviating from the scope of the present embodiment. It is also understood that the binding molecule can provide the requisite nucleophilic and electrophilic functional groups. For example, where the binding molecule is a protein, the nucleophilic and electrophilic functional groups may be present as naturally occurring amino acids in the protein, or may be introduced to the protein using chemical techniques described herein.

Other general methods for preparing or crosslinking polymers to form matrices such as hydrogels are well known in the art. For example, Ghandehari H., et al., J. Macromol. Chem. Phys. 197: 965 (1996); and Ishihara K, et al., Polymer J., 16: 625 (1984), all of which are hereby incorporated by reference, report the formation of hydrogels. Hydrogel matrix can be applied to each sensor tip, e.g., a needle, and cured under a Hg lamp, with wavelength of >360 nm, for about 15 seconds.

The thermostable GGBPs can be covalently attached to or non-covalently entrapped or encapsulated within a matrix, such as, but not limited to, a hydrogel. In one embodiment of the present invention, the binding molecules are covalently attached to, i.e., entrapped within, a hydrogel. The covalent attachment of the binding molecule to the hydrogel should not interfere with the binding of the binding molecule to the target ligand. Furthermore, the covalent attachment of the binding molecule to the hydrogel should be resistant to degradation. The functional group in one embodiment is a polymer or other component of the hydrogel that serves to couple the binding molecule to the hydrogel. The coupling of the binding molecule to the hydrogel can be accomplished in any number of ways. For example, coupling reactions between the hydrogel and binding molecule include, but are not limited to, diazonium coupling, isothiocyano coupling, hydrazide coupling, amide formation, disulfide coupling, maleic anhydride coupling, thiolactone coupling, and dichlotriazine coupling. These coupling reactions between two functional groups are well documented, and are considered well known to those skilled in the art. For example, an amino functional group in a binding molecule can be covalently coupled to a carboxyl functional group of one or more components of a hydrogel using coupling agents such as 1-ethyl-3-(3-dimethylaminopropyl)carbodiimide hydrochloride (EDC) or dicyclohexylcarbodiimide (DCC). It is understood that the amino and carboxyl functional groups of the binding molecule and one or more components of the hydrogel as described above can be transposed without deviating from the scope of the embodiment.

In one embodiment, the matrix comprises polyethyleneglycol dimethacrylate (PEGDMA) and methacrylic acid (MAA). The ratio of PEGDMA to MAA may vary among specific embodiments. In one embodiment the ration of PEGDMA:MAA can range from about 10:90 mol % to about 90:10 mol %. In one specific embodiment, the ratio of PEGDMA:MAA is about 20:80 mol %. In another specific embodiment, the ratio of PEGDMA:MAA is about 21:79 mol %. In another specific embodiment, the ratio of PEGDMA:MAA is about 23:77 mol %. In another specific embodiment, the ratio of PEGDMA:MAA is about 25:75 mol %. In another specific embodiment, the ratio of PEGDMA:MAA is about 27:73 mol %. In another specific embodiment, the ratio of PEGDMA:MAA is about 29:71 mol %. In another specific embodiment, the ratio of PEGDMA:MAA is about 30:70 mol %. In another specific embodiment, the ratio of PEGDMA:MAA is about 35:65 mol %. In another specific embodiment, the ratio of PEGDMA:MAA is about 40:60 mol %. In another specific embodiment, the ratio of PEGDMA:MAA is about 42:58 mol %. In another specific embodiment, the ratio of PEGDMA:MAA is about 44:56 mol %. In another specific embodiment, the ratio of PEGDMA:MAA is about 46:54 mol %. In another specific embodiment, the ratio of PEGDMA:MAA is about 48:52 mol %. In another specific embodiment, the ratio of PEGDMA:MAA is about 50:50 mol %. Initiators, such as HMPP, may also be present in various concentrations in the hydrogel. For example, photoinitiators may be present in concentrations from about 0.10% to about 5% total volume. In one embodiment, the photoinitiator is present in concentrations of from about 0.1% to about 1%. In a specific embodiment, the photoinitiator is present at least about 0.20% total volume. In a specific embodiment, the photoinitiator is present at least about 0.25% total volume. In a specific embodiment, the photoinitiator is present at least about 0.30% total volume. In a specific embodiment, the photoinitiator is present at least about 0.35% total volume. In a specific embodiment, the photoinitiator is present at least about 0.40% total volume.

As discussed herein, the biosensors of the present invention may comprise the thermostable GGBPs entrapped in a polymeric matrix, that is, in turn, contained within a needle tip. Some sensors, such as subcutaneous implants, typically demonstrate a lag time. In particular, larger gauge sensors, i.e., 21 and 25, gauge are too large to accurately read in shallow skin depths. Shallow depth skin tissue glucose levels appear to have little, if any, time lag when compared to the glucose value in blood. This shallow depth penetration enables the sampling of interstitial fluids for accurate glucose concentrations levels, with almost no lag time. In one embodiment, therefore, the needle of the biosensor is a 31 gauge needle or smaller that is capable of penetrating a subject's skin at shallow depths, e.g., less than about 2 mm, less than about 1 mm, or even less than about 0.8 mm, nad providing accurate glucose readings with little or no time lag.

The invention also relates to devices comprising the thermostable GGBPs of the present invention. The devices, in general, comprise: (i) an optical conduit having a proximal end and a distal end; and (ii) a sensing element in optical proximity to the distal end of the optical conduit that comprises at least one of the thermostable GGBPs of the present invention and at least one reporter group.

The optical conduit, which may vary in length from approximately 0.1 cm to 1 meter, couples light into and out of an optical system and into and out of the sensing element. For example, the optical conduit may be a lens, a reflective channel, a needle, or an optical fiber. The optical fiber may be either a single strand of optical fiber (single or multimode) or a bundle of more than one fiber. In one embodiment, the bundle of fibers is bifurcated. The fiber may be non-tapered or tapered so that it can penetrate the skin of a patient.

An optical system may be connected to the proximal end of the optical conduit. The optical system consists of a combination of one or more excitation sources and one or more detectors. It may also consist of filters, dichroic elements, a power supply, and electronics for signal detection and modulation. The optical system may optionally include a microprocessor.

The optical system interrogates the sample either continuously or intermittently by coupling one or more interrogating wavelengths of light into the optical conduit. The one or more interrogating wavelengths then pass through the optical conduit and illuminate the sensing element. A change in analyte concentration may result in a change of the wavelength, intensity, lifetime, energy transfer efficiency, and/or polarization of the luminescence of the reporter group, which is a part of the sensing element. The resulting changed luminescence signal passes back through the optical conduit to the optical system where it is detected, interpreted, and stored and/or displayed. In certain embodiments, the optical system comprises multiple excitation sources. One or more of these sources may be modulated to permit dynamic signal processing of the detected signal, thereby enhancing signal-to-noise and detection sensitivity. Modulation may also be used to reduce power consumption by the device or to increase the lifetime of the sensing element by minimizing undesirable phenomena such as photobleaching. The optical system can also include one or more electromagnetic energy detectors that can be used for detecting the luminescence signal from the reporter and optional reference groups as well as for internal referencing and/or calibration. The overall power consumption of the optical system is kept small to permit the device to be operated using battery power.

The following examples are illustrative and are not intended to limit the scope of the invention described herein.

EXAMPLES

Example 1

Construction and Production of Modified Thermostable GGBPs

Amino acid residues of the GGBP termed "3M-GGBP" (SEQ ID NO:3), including several asparagine and glutamine residues, were selected for substitution based on their a consensus alignment of similar amino acid sequences in wild-type E. coli GGBP (SEQ ID NO:1) as determined by a BLASTP search. In particular, the following 21 amino acids of 3M-GGBP were selected for substitution: asparagine 39 (N39), aspartic acid 50 (D50), glutamine 51 (Q51), glycine 82 (G82), glutamine 83 (Q83), asparagine 84 (N84), asparagine 130 (N130), glutamine 175 (Q175), glutamine 177 (Q177), leucine 178 (L178), glycine 198 (G198), proline 199 (P199), asparagine 200 (N200), asparagine 226 (N226), asparagine 259 (N259), asparagine 260 (N260), lysine 270 (K270), asparagine 271 (N271), asparagine 283 (N283), tryptophan 284 (W284) and asparagine 302 (N302).

Each of the 21 selected residues of 3M-GGBP was then separately substituted to create 13 initial modified GGBPs. Alignments of proteins with similar amino acid sequences to wild-type E. coli GGBP (SEQ ID NO:1) as determined by a BLASTP search was used to determine the identity of the replacement amino acid (see Table I). Modified 3M-GGBPs were generated in the 3M-GGBP construct using the QUIKCHANGE™ method (Stratagene). Oligonucleotides were designed to replace targeted residues with other amino acids. In some cases, the oligonucleotides were designed to replace up to three amino acids at a particular locus, e.g., G82, Q83, and N84. Using a standard reaction mixture, PCR, and the designed oligonucleotides, mutations were made in the template 3M-GGBP plasmid. After PCR, the product was digested with DpnI and transformed into E. coli according to the QUIKCHANGE™ protocol. After transformation into E. coli, plasmid DNA was purified and the desired sequence change was verified by DNA sequencing. Each of the thirteen modifications, shown in Table I below, was generated and verified in this manner, creating a DNA template for a modified 3M-GGBP.

In a similar fashion, amino acids of a GGBP termed "W183C" (SEQ ID NO:4) can be modified. In particular, the following 21 amino acids of W183C are selected for substitution: asparagine 39 (N39), aspartic acid 50 (D50), glutamine 51 (Q51), glycine 82 (G82), glutamine 83 (Q83), asparagine 84 (N84), asparagine 130 (N130), glutamine 175 (Q175), glutamine 177 (Q177), leucine 178 (L178), glycine 198 (G198), proline 199 (P199), asparagine 200 (N200), asparagine 226 (N226), asparagine 259 (N259), asparagine 260 (N260), lysine 270 (K270), asparagine 271 (N271), asparagine 283 (N283), tryptophan 284 (W284) and asparagine 302 (N302).

The same substitutions that were placed into the 3M-GGBP, above, were chosen as substitutions for modifying the W183C. Modified W183Cs were generated in the W183C construct using the QUIKCHANGE™ method (Stratagene). Using a standard reaction mixture, PCR, and the designed oligonucleotides, modifications were made in the template 3M-GGBP plasmid. After PCR, the product was digested with DpnI and transformed into E. coli according to the QUIKCHANGE™ protocol. After transformation into E. coli, plasmid DNA was purified and the desired sequence change was verified by DNA sequencing.

The modified GGBP were expressed from E. coli strain Sg13009 following standard protocols (Qiagen). After induction, bacteria were lysed using Bugbuster protein extraction reagent (Novagen) and purified by IMAC using Talon cobalt$^{2+}$ resin (Clontech). The purified protein in solution was filtered through 100 kDa cutoff filter and then concentrated using a 10 kDa cutoff filter (Millipore). The protein (1-2 mg/ml) was dialyzed at 4° C. into a solution containing 1M NaCl, 10 mM Tris-HCl, and 50 mM NaPO$_4$ (pH 8) and stored at 4° C. Under these conditions the protein was active for at least six months. The yield from the purification was approximately 10 mg/l.

TABLE I

| | Modification(s) |
|---|---|
| 1 | N39I |
| 2 | D50K, Q51H |
| 3 | G82E, Q83K, N84D |
| 4 | N130D |
| 5 | Q175E, Q177H, L178M |
| 6 | Q175I, Q177E |
| 7 | G198S, P199S, N200K |
| 8 | N226G |
| 9 | N226K |
| 10 | N259E, N260S |
| 11 | K270Y, N271S |
| 12 | N283D, W284L |
| 13 | N302T |

Example 2

Determining the Melting Temperature of the Modified GGBPs

Circular Dichroism (CD) spectra were preformed on a JASCO J-810. Samples of purified fluorophore-labeled proteins were exhaustively dialyzed into phosphate buffered saline (PBS) (comprised of 137 mM NaCl, 10 mM phosphate and 2.7 mM KCl, pH 7.4). The loss of secondary structure of 3M-GGBP and W183C-GGBP was observed by recording the CD signal at 222 nm as a function of temperature. During the experiment, the temperature of the sample changed at a rate of ~1° C./min between 20 and 80° C. The apparent melting temperature at the midpoint of the transition (Tm) was obtained by fitting the experimental data points (CD signal versus temperature) with a sigmoidal function.

Table II below depicts the results from the circular dichroism study of each of the thirteen modified GGBPs. Modified proteins 1, 3, 5 and 10 had the greatest increase of $T_m$ over the reference protein.

TABLE II

| No. | Modification(s) | +ΔTm | −ΔTm |
|---|---|---|---|
| 1 | N39I | 1 | |
| 2 | D50K, Q51H | ND | ND |
| 3 | G82E, Q83K, N84D | 1.5 | |
| 4 | N130D | | 5.2 |
| 5 | Q175E, Q177H, L178M | 3 | |
| 6 | Q175I, Q177E | | 0.3 |
| 7 | G198S, P199S, N200K | 0.5 | |
| 8 | N226G | 0.9 | |
| 9 | N226K | 0.3 | |
| 10 | N259E, N260S | 3.6 | |
| 11 | K270Y, N271S | | 3.5 |
| 12 | N283D, W284L | | 3.7 |
| 13 | N302T | | 0.2 |

Example 3

Constructing a Modified Thermostable GGBP with Multiple Amino Acid Substitutions Based on the results from Example 2, two separate modified GGBPs were constructed comprising the residue substitution numbers N39I, G82E, Q83K, N84D, Q175E, Q177H, L178M, N259E and N260S from the previous example. In this example, the two reference proteins were 3M-GGBP and W183C. Both modified proteins were constructed as in Example 1. Briefly, a construct encoding a substituted locus was constructed and DNA was sequenced for verification. Plasmid DNAs were then used as the template DNAs to add the substituted locus, thus generating a plasmid DNA vectors coding for either 3M-GGBP protein (SEQ ID NO:3), or W183C (SEQ ID NO:4), except that each sequence comprised substitutions corresponding to N39I, G82E, Q83K, N84D, Q175E, Q177H, L178M, N259E and N260S.

Example 4

Labeling the Modified Thermostable GGBP

The SM4 protein, which is W183C with mutations 1, 3, 5 and 10 (see Table I) was labeled with a fluorescent entity (acrylodan), and 3M-GGBP was mutations 1, 3, 5 and 10 from Table I was labeled with a fluorescent entity (IANBD) using the methods as described in United States Patent Publication No. 2005/0112685, published 26 May 2005, which is incorporated by reference.

The SM4 was labeled in the following manner. Dimethylsulfoxide (DMSO—6.14 mL) was added to a solution (100 mg in 60.3 mL PBS, pH 7.4) of the modified GGBP protein of Example 5 (with the affinity tags). An aliquot of 565 µL of 12 mM acrylodan in DMSO was then added to the solution. The final percentage of DMSO in the solution was about 10%. The flask was wrapped in aluminum foil and was stirred for 4 h at room temperature. The reaction mixture was then centrifuged for 10 min at 26,712 RCF (relative centrifugal force). The supernatant was removed and passed through a 5 µm Supor filter (Pall Corporation, East Hills, N.Y., USA).

After labeling with acrylodan the SM4 was transferred to a buffer for frozen storage. The protein was dialyzed against a solution of 0.01M MES, 30 mM glucose (pH 5.5-5.7) for 24 h with three changes of buffer. After dialysis the protein was quantified and diluted to a 100 µM solution using the same buffer. The vials were then placed directly into a −70° C. freezer for storage. The protein is stable for at least 3 months under these conditions.

To lyophilize the SM4 protein, the protein solution was dialyzed against ammonium bicarbonate (50 mM, pH 7) for 24 h with three changes of buffer. The protein was passed through a 0.2 um Supor filter (Pall) and was aliquoted into amber vials (2 mg/vial). The vials were frozen at −70° C. for 3 h, and then the protein was lyophilized for 20 h. The final yield was about 86 mg of protein with a dye/protein ratio of about 0.94. The protein is stable for at least 6 months under these conditions. For frozen storage the protein the protein solution was dialyzed against The protein was dialyzed against a solution of 0.01M MES (2-(N-Morpholino)ethanesulfonic acid), 30 mM glucose (pH 5.5-5.7) for 24 h with three changes of buffer. The protein was frozen and stored at −70° C.

Example 5

Determining the Melting Temperature of the Modified and Labeled GGBPs

Using the same protocol as in Example 2, the melting temperatures of the modified GGBPs (modified 3M-GGBP and W183C) prepared in Example 3 were determined. The measured $T_m$ of the modified W183C-GGBP was about 9.4° C. greater than that of the reference protein (W183C) (FIG. 1). Similarly, modified 3M-GGBP having substitution numbers 1, 3, 5 and 10 from Table I above displayed a higher $T_m$. Table III below shows the increase in $T_m$ for the two modified GGBPs of the present invention.

TABLE III

Thermal Stability of Modified GGBPs

| Protein | Tm* | Kd | Fluorescent Response | Dye/Protein |
|---|---|---|---|---|
| W183C-acrylodan | 39.8 ± 2% | 19.6 ± 10% | 3.4 ± 8% | 1.1 ± 30% |
| W183C(1,3,5,10)-acrylodan | 49.2 ± 1% | 21.7 ± 6% | 4.7 ± 5% | 1.1 ± 10% |
| 3M-IANBD | 45.4 ± 1% | 9.6 | 11 | 0.9 |
| 3M(1,3,5,10)-IANBD | 52.9 ± 2% | 13.6 | 12.1 | 1.0 |

*Tm determined in PBS

Example 6

Modified GGBPs with an Affinity Tag

The SM4 protein was cloned into a vector that produces large protein yields (6-7 g/L). This vector places an additional 30 residues onto the W183C(1,3,5,10) protein for affinity purification and conjugation purposes. The vector adds the amino acid sequence MGHNHNHNHNHNHNGGDDDDK (SEQ ID NO:5), in an N-terminus to C-terminus direction, on the N-terminus and the amino acid sequence GGKKKKKKKEE (SEQ ID NO:6), in an N-terminus to C-terminus direction, on the C-terminus of the polypeptide. The melting temperature of this protein, with the termini additions present, was determined to be about 53° C. in PBS (with 0.1 g/L of CaCl$_2$ (anhydrous) and 0.1 g/L MgCl$_2$-6H$_2$O). On the other hand, the melting temperature of this protein, without the termini additions present, was determined to be about 55.4° C. in PBS. Glucose affinity of SM4 with termini additions was measured as 19.6 mM and the fluorescent response (Qr) was measured as 4.8.

Example 7

Measuring Analyte Concentrations Using the Labeled Modified Thermostable GGBP For the modified, thermostable 3M and W183C proteins, a fluorescence assay as disclosed in Looger, L. L., et al., Nature, 423:185-189 (2003) (incorporated by reference), was used to verify the glucose binding activity of the proteins. Dye-protein fluorophore (N,N'-dimethyl-N-(iodoacetyl)-N'-(7-nitrobenz-2-oxa-1,3-diazol-4-yl)ethylenediamine designated IANBD) or acrylodan coupling was performed as described by the manufacturer (Molecular Probes).

Briefly, 0.5 ml of 3M-GGBP (1-2 mg/ml) was treated with 2.5 molar excess of dithiothreitol for 30 min. A 10-fold molar excess solution of IANBD in DMSO (0.5 mg/100 uL) was then added. While protected from light, the protein and dye were gently mixed for 4 h at 25° C. before the unreacted dye was removed by Nap-5 column chromatography (Amersham Biosciences).

The efficiency of the coupling was determined by absorbance:

$$\frac{A_x}{\epsilon} \times \frac{MW_p}{mg_p/ml} = \frac{mole_d}{mole_p}$$

Where $A_x$ is the absorbance value of the dye at the absorption maximum wavelength and E is the molar extinction coefficient of the dye at the absorption maximum. $MW_p$, $mg_p$/ml, and $mole_p$ are the molecular weight, concentration, and molar amount of the protein, respectively. The molar amount of dye is $mole_d$.

Binding constants were determined by titration of increasing concentrations of glucose into a 0.1 μM protein in PBS and monitoring the change in fluorescence. The $K_d$ was determined from the following relationships as adapted from Pisarchick and Thompson (Pisarchick, M. L. and Thompson, N. L. *Biophys. J.* (1990), 58, 1235-1249):

$$F = F_{inf} + \frac{F_0 - F_{inf}}{1 + x/K_d}$$

where F is fluorescence intensity, $F_{inf}$ is fluorescence at infinity, $F_0$ is fluorescence at zero $$[Glc]_{free} = \frac{[Glc]_{tot} - [Prot]_{tot} - K_d + \sqrt{([Glc]_{tot} - [Prot]_{tot} - K_d)^2 + 4*[Glc]_{tot}*K_d}}{2}$$

where $[Glc]_{free}$ is the concentration of free glucose and $[Glc]_{tot}$ and $[Prot]_{tot}$ are the total concentrations of glucose and protein, respectively. For the SM4, the ratio of the area under the fluorescence curve from 514-540 nm to the area under the curve at 450-470 nm was used in place of fluorescence intensity in the equations above. The current invention, however, is not limited to particular wavelength region of fluorescence when measuring fluorescence or evaluating glucose concentrations.

Figure 2:
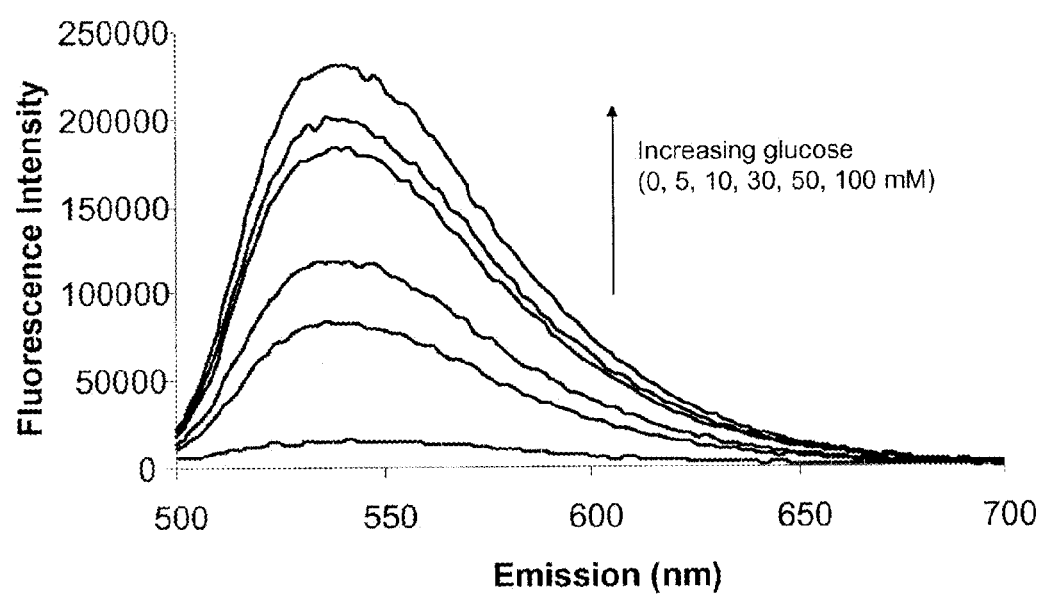
FIG. 2 depicts the emission spectrum of modified thermostable 3M-GGBP in increasing concentrations of glucose.

The results of binding experiments have demonstrated that the acrylodan-labeled SM4, produced according to Example 3, also had increased fluorescence response as compared to the reference W183C-acrylodan (see Table III). FIG. 2 shows the increase in fluorescence intensity upon titration of 3M-GGBP (1,3,5,10) labeled with IANBD using increasing concentrations of glucose (0, 5, 10, 30, 50, and 100 mM).

Example 8

Liquid Chromatography Fourier Transform Mass Spectroscopy (LC-FTMS) to Quantify Deamidaton at Select Residues of GGBP To identify additional deamidation sites, liquid chromatographic-Fourier Transform MS (LC-FTMS) was used to quantify deamidation at the asparagine residues in W183C and SM4. W183C and SM4 (from Example 5) were either kept at 25° C. or heat treated (18 hours at 60° C.) prior to trypsin digestion. Peptides were then separated using a 15 cm Pep-Map C18 capillary column (75 micron id) with a 30 minute gradient from about 5% to about 95% acetonitrile and analyzed by LC-FTMS. Deamidation leads to a mass shift of approximately 1 dalton. Samples were examined for deamidation doublets and were reported as relative deamidation peak ratios where a smaller ratio indicates greater deamidation of the resudues. Table IV shows the relative deamidation levels of the residues of the peptide sequences, with the smaller number indicating a greater level of deamidation. Table V shows potential amino acid substitutions identified by the quantitative deamidation process.

TABLE IV

Deamidation Quantified by LC-FTMS

| Peptide Sequences Identified by FT-MS | | Relative Deamidation | | | | See - Table II Previously Tested | |
|---|---|---|---|---|---|---|---|
| | | W183C | | W183C(1, 3, 5, 10) | | | |
| W183C | W183C(1, 3, 5, 10) | 25° C. | 60° C. | 25° C. | 60° C. | No. | ΔTm |
| AAPDVQLLMN*DSQN*DQSK (SEQ ID NO: 7) | AAPDVQLLMI* DSQ N* DQSK (SEQ ID NO: 14) | 3.20 | 1.00 | 7.90 | 1.92 | 1 | +1 |
| DKMDAWLSGPN*AN*K (SEQ ID NO: 8) | DKMDAWLSGPN*AN*K (SEQ ID NO: 8) | 3.43 | 0.86 | | 1.16 | 7 | +0.5 |

TABLE IV-continued

Deamidation Quantified by LC-FTMS

| Peptide Sequences Identified by FT-MS | | Relative Deamidation | | | | See - Table II Previously Tested | |
|---|---|---|---|---|---|---|---|
| | | W183C | | W183C(1, 3, 5, 10) | | | |
| W183C | W183C(1, 3, 5, 10) | 25° C. | 60° C. | 25° C. | 60° C. | No. | ΔTm |
| HWAAN*QGWDLN*K (SEQ ID NO: 9) | HWAAN*QGWDLN*K (SEQ ID NO: 9) | | | | 6.9 | 4 | -5.2 |
| ATFDLAKN*LADGK (SEQ ID NO: 10) | ATFDLAKN*LADGK (SEQ ID NO: 10) | | 1.42 | | | | |
| GAADGTN*WK (SEQ ID NO: 11) | GAADGTN*WK (SEQ ID NO: 11) | | | | 2.5 | 11 | -3.5 |
| YDDN*FMSVVR (SEQ ID NO: 12) | YDDN*FMSVVR (SEQ ID NO: 12) | 11.51 | 6.01 | 1.7 | | | |
| QN*DQIDVLLAK (SEQ ID NO: 13) | QN*DQIDVLLAK (SEQ ID NO: 13) | 3.05 | 1.09 | 4.79 | 5.19 | 12 | -3.7 |

Note:
asparagines (N) are starred, mutations are underlined and mutations replacing an N residue are starred and underlined

TABLE V

| W183C(1, 3, 5, 10) Peptide Sequence | Previously Tested Mutations | No | Peptide Sequence | New Mutations |
|---|---|---|---|---|
| AAPDVQLLM I* DSQN*DQSK (SEQ ID NO: 14) | APPDVQLLM I* DSQN*DQSK (SEQ ID NO: 14) | 1 | AAPDVQLLM I* DGQG*DQSK (SEQ. ID NO: 19) AAPDVQLLM I* DSQA*DQSK (SEQ. ID NO: 20) | N39I, S41G, N43G N39I, N43A |
| DKMDAWLSGPN*AN*K (SEQ ID NO: 8) | DKMDAWLSSSK*ANK (SEQ ID NO: 15) | 7 | DKMDAWLSSGK*A**K*D** (SEQ ID NO: 21) | G198S, P199G, N200K, N202K, K203D |
| HWAAN*QGWDLN*K (SEQ ID NO: 9) | HWAADQGWD*L**N*K (SEQ ID NO: 16) | 4 | HWKAD*PTLDLNK (SEQ ID NO: 22) HWKAD*PTLDLNK (SEQ ID NO: 22) | A128K, N130D, Q131P, G132T, W133L A128K, A129S, N130S, Q131E, G132A W133L |
| ATFDLAKN*LADGK (SEQ ID NO: 10) | ATFDLAYS*LADGK (SEQ ID NO: 17) | 11 | ATFDFSRL*LADGK (SEQ ID NO: 23) ATFELARL*LADGK (SEQ ID NO: 24) | L268F, A269S, K270R, N271L D267E, K270R, N271L |
| GAADGTN*WK (SEQ ID NO: 11) | GAADGTD*LK (SEQ ID NO: 18) | 12 | GAADGTM*PK (SEQ ID NO: 25) | N283M, W284P |
| YDDN*FMSVVR (SEQ ID NO: 12) | | | FDDT*FMSVVR (SEQ ID NO: 26) | Y12F, N15T |
| QN*DQIDVLLAK (SEQ ID NO: 13) | | | Q I* E Q V DVLLAK (SEQ ID NO: 27) | N49I, D50E, I52V |

Note:
asparagines (N) are starred, mutations are underlined and mutations replacing an N residue are starred and underlined

---

What is claimed is:

1. A nucleic acid encoding a modified thermostable glucose-galactose binding protein (GGBP), wherein the modified GGBP is capable of binding glucose and comprises one or more residue substitutions selected from the group consisting of N39I, G82E, Q83K, N84D, Q175E, Q177H, L178M, N259E and N260S of SEQ ID NO: 4.

2. The nucleic acid of claim 1, wherein the modified GGBP comprises the substitutions N39I, G82E, Q83K, N84D, Q175E, Q177H, L178M, N259E and N260S.

3. A vector comprising a nucleic acid encoding a modified thermostable glucose-galactose binding protein (GGBP), wherein the modified GGBP is capable of binding glucose and comprises one or more residue substitutions selected from the group consisting of N39I, G82E, Q83K, N84D, Q175E, Q177H, L178M, N259E and N260S of SEQ ID NO: 4.

4. The vector of claim 3, wherein the vector is an expression vector.

5. A host cell comprising an expression vector comprising a nucleic acid encoding a modified thermostable glucose-galactose binding protein (GGBP), wherein the modified GGBP is capable of binding glucose and comprises one or more residue substitutions selected from the group consisting of N39I, G82E, Q83K, N84D, Q175E, Q177H, L178M, N259E and N260S of SEQ ID NO: 4.

6. A method of making a modified thermostable GGBP, said method comprising culturing the host cell of claim 5 in conditions suitable for protein expression and isolating said protein.

7. A vector comprising a nucleic acid encoding a modified thermostable glucose-galactose binding protein (GGBP), wherein the modified GGBP is capable of binding glucose and comprises substitutions N39I, G82E, Q83K, N84D, Q175E, Q177H, L178M, N259E and N260S of SEQ ID NO: 4.

8. The vector of claim 7, wherein the vector is an expression vector.

9. A host cell comprising an expression vector comprising a nucleic acid encoding a modified thermostable glucose-galactose binding protein (GGBP), wherein the modified GGBP is capable of binding glucose and comprises substitutions N39I, G82E, Q83K, N84D, Q175E, Q177H, L178M, N259E and N260S of SEQ ID NO: 4.

10. A method of making a modified thermostable GGBP, said method comprising culturing the host cell of claim 9 in conditions suitable for protein expression and isolating said protein.

\* \* \* \* \*